US012049661B2

(12) United States Patent
Liu et al.

(10) Patent No.: US 12,049,661 B2
(45) Date of Patent: Jul. 30, 2024

(54) **CONSTRUCTION AND APPLICATION OF ENGINEERED STRAIN OF *ESCHERICHIA COLI* FOR PRODUCING MALIC ACID BY FIXING $CO_2$**

(71) Applicant: Jiangnan University, Wuxi (CN)

(72) Inventors: Liming Liu, Wuxi (CN); Guipeng Hu, Wuxi (CN); Xiulai Chen, Wuxi (CN); Danlei Ma, Wuxi (CN); Jia Liu, Wuxi (CN); Qiuling Luo, Wuxi (CN)

(73) Assignee: JIANGNAN UNIVERSITY, Wuxi (CN)

( * ) Notice: Subject to any disclaimer, the term of this patent is extended or adjusted under 35 U.S.C. 154(b) by 507 days.

(21) Appl. No.: 17/479,018

(22) Filed: Sep. 20, 2021

(65) Prior Publication Data

US 2022/0002766 A1    Jan. 6, 2022

Related U.S. Application Data

(63) Continuation of application No. PCT/CN2019/127756, filed on Dec. 24, 2019.

(30) Foreign Application Priority Data

Dec. 19, 2019  (CN) .......................... 201911317890.8

(51) Int. Cl.
  *C12P 7/46* (2006.01)
  *C12N 1/20* (2006.01)
  (Continued)

(52) U.S. Cl.
  CPC ................. *C12P 7/46* (2013.01); *C12N 1/20* (2013.01); *C12N 9/0006* (2013.01); *C12N 9/001* (2013.01);
  (Continued)

(58) Field of Classification Search
  CPC ........... C12P 7/46; C12N 1/20; C12N 9/0006; C12N 9/001; C12N 9/0093; C12N 9/1205;
  (Continued)

(56) References Cited

U.S. PATENT DOCUMENTS 8,129,154 B2 *  3/2012  Burk .......................... C12P 7/46
                                                           435/145
2004/0091985 A1 *  5/2004  Metcalf .................. C12P 19/36
                                                           435/189

(Continued)

FOREIGN PATENT DOCUMENTS

CN       1246155 A      3/2000
CN     101255405 A      9/2008
(Continued)

OTHER PUBLICATIONS

Dong et al.,Metabolic Engineering of *Escherichia coli* W3110 to Produce L-Malate, Biotech. And Bioengineering, vol. 114, No. 3, Mar. 2017, p. 656-664 (Year: 2017).*

(Continued)

*Primary Examiner* — Soren Harward
*Assistant Examiner* — Naghmeh Nina Moazzami
(74) *Attorney, Agent, or Firm* — IPRO, PLLC

(57) ABSTRACT

The disclosure discloses construction and application of an engineered strain of *E. coli* for producing malic acid by fixing $CO_2$, and belongs to the field of fermentation. The engineered strain is obtained by performing genetic engineering transformation on *Escherichia coli* MG1655; the genetic engineering transformation includes knocking out a fumarate reductase gene, a fumarase gene, a lactate dehydrogenase gene and an alcohol dehydrogenase gene and freely overexpressing a formate dehydrogenase, an acetyl coenzyme A synthetase, an acylated acetaldehyde dehydrogenase, a formaldehyde lyase, a dihydroxyacetone kinase, a
(Continued)

malic enzyme and a phosphite oxidoreductase to obtain a strain GH0407. The strain is used for producing malic acid by fermentation, anaerobic fermentation is performed for 72 hours with $CO_2$ and glucose as a co-substrate, the production of malic acid reaches 39 g/L, the yield is 1.53 mol/mol, and accumulation of malic acid in the original strain is not achieved.

8 Claims, 4 Drawing Sheets

Specification includes a Sequence Listing.

(51) Int. Cl.
  *C12N 9/00* (2006.01)
  *C12N 9/02* (2006.01)
  *C12N 9/04* (2006.01)
  *C12N 9/12* (2006.01)
  *C12N 9/88* (2006.01)
  *C12N 15/70* (2006.01)

(52) U.S. Cl.
  CPC ......... *C12N 9/0093* (2013.01); *C12N 9/1205* (2013.01); *C12N 9/88* (2013.01); *C12N 9/93* (2013.01); *C12N 15/70* (2013.01); *C12Y 101/01001* (2013.01); *C12Y 101/01028* (2013.01); *C12Y 101/0104* (2013.01); *C12Y 103/05004* (2013.01); *C12Y 117/01* (2013.01); *C12Y 207/01029* (2013.01); *C12Y 402/01002* (2013.01); *C12Y 602/01001* (2013.01)

(58) Field of Classification Search
  CPC . C12N 9/88; C12N 9/93; C12N 15/70; C12N 15/52; C12N 9/0004; C12N 9/0008; C12N 9/1029; C12Y 101/01001; C12Y 101/01028; C12Y 101/0104; C12Y 103/05004; C12Y 117/01; C12Y 207/01029; C12Y 402/01002; C12Y 602/01001; C12Y 102/0101; C12Y 120/01001; C12Y 101/01027; C12Y 102/01002; C12R 2001/19

See application file for complete search history.

(56) References Cited

U.S. PATENT DOCUMENTS

| | | | | |
|---|---|---|---|---|
| 2006/0183193 | A1* | 8/2006 | Horanyi | C12N 15/70 435/325 |
| 2010/0248233 | A1* | 9/2010 | Muller | C07K 14/33 435/254.2 |
| 2014/0325709 | A1* | 10/2014 | Plesch | C07K 14/245 426/531 |
| 2016/0215274 | A1* | 7/2016 | Shaw | C12N 9/0004 |

FOREIGN PATENT DOCUMENTS

| | | |
|---|---|---|
| CN | 104046577 A | 9/2014 |
| CN | 104694449 A | 6/2015 |
| CN | 106434772 A | 2/2017 |
| WO | 2012031079 A2 | 3/2012 |

OTHER PUBLICATIONS

Seigel et al., Computational protein design enables a novel one-carbon assimilation pathway, Proc Natl Acad Sci U S A. Mar. 24, 2015;112(12):3704-9. (Year: 2015).*

Li et al.,Metabolic engineering of *Escherichia coli* for the production of L-malate from xylose, Metabolic Engineering, vol. 48, 2018, p. 25-32. (Year: 2018).*

Khankal et al., Comparison between *Escherichia coli* K-12 strains W3110 and MG1655 and wild-type *E. coli* B as platforms for xylitol production (2008) Biotechnol Lett 30, 1645-1653 (Year: 2008).*

Dong, Xiaoxiang, "Design and construction of L-malate overproducing *Escherichia coli* strains" China Excellent Master's Thesis Full-text Database Engineering Science and Technology,Feb. 15, 2017), 1-10, B018-256 p. 1-40.

Wu, Yabin, "the Construction and fermentation of recombinant *E. coli.* for L-malic acid production" China Excellent Master's Thesis Full-text Database Engineering Science and Technology,Apr. 15, 2013, 1-10,B018-88 1-41.

X. Zhang et. al. "L-Malate Production by Metabolically Engineered *Escherichia coli*"Applied and Environmental Microbiology, vol. 77 No. 2, Jan. 2011, p. 427 434.

* cited by examiner

CONSTRUCTION AND APPLICATION OF ENGINEERED STRAIN OF *ESCHERICHIA COLI* FOR PRODUCING MALIC ACID BY FIXING CO₂

TECHNICAL FIELD

The disclosure relates to construction and application of an engineered strain of *Escherichia coli* for producing malic acid by fixing $CO_2$, and belongs to the field of fermentation engineering.

BACKGROUND

With constant increase of concentration of $CO_2$ in the atmosphere, global climate changes are affected; therefore, it is urgent to develop an effective $CO_2$ storage technology to improve capture of $CO_2$ or reduce release of $CO_2$. Traditional carbon dioxide storage technologies based on physical and chemical methods include carbon dioxide capture (such as post-combustion and oxyfuel combustion), carbon dioxide separation (such as adsorption and membrane separation) and carbon dioxide storage (such as saline aquifers and offshore geological structures) and have great significance in reduction of carbon dioxide. However, these methods have some obvious shortcomings, such as high energy consumption, high operating costs or production of degradation products harmful to human health and the environment. Compared with these methods, $CO_2$ storage with microorganisms is an environmentally friendly way to alleviate the greenhouse effect, and at the same time, chemicals with high added values can be produced.

$CO_2$ fixation with heterotrophic microorganisms may be divided into three levels: (i) directly improving an endogenous carboxylation reaction in the heterotrophic microorganisms; (ii) constructing artificially synthesized $CO_2$ fixation branches in the heterotrophic microorganisms and ligating the $CO_2$ fixation branches to central carbon metabolism; (iii) transforming the heterotrophic microorganisms so that the heterotrophic microorganisms can grow with $CO_2$ as the only carbon source. The first level has a significant defect that only a few special compounds can be produced and $CO_2$ cannot be fixed for products without the carboxylation reaction in a synthetic route, the third level has not been fully realized at present, and the best research progress at present is that a semi-autotrophic *E. coli* strain is obtained. Therefore, in order to better produce chemicals by fixing $CO_2$ with heterotrophic microorganisms, $CO_2$ fixation pathways need to be artificially constructed and ligated to an upstream of glycolysis, so that the purposes of high $CO_2$ fixation efficiency and broad product spectrum are achieved.

As an important four-carbon platform compound, L-malic acid has been listed as one of basic compounds by the Department of Energy in the United States and is applied in the fields of food, medicine, chemical engineering and other industries. In the field of food, L-malic acid has become the third food acidulant with consumption after citric acid and lactic acid; in the field of medicine, L-malic acid directly participates in human metabolism and has the effects of preventing fatigue, protecting liver, kidney and heart and reducing toxic and side effects of anti-cancer drugs; in the field of chemical engineering, L-malic acid is used in production of daily cosmetics, cleaning and finishing of metals, finishing of fabrics, chemical plating and the like. L-malic acid is an important intermediate metabolite in cycle of tricarboxylic acid, and malic acid cannot be detected in a fermentation solution of wild-type *E. coli* (lower than a detection limit of HPLC).

SUMMARY

A first objective of the disclosure is to provide an engineered strain of *E. coli* capable of fixing $CO_2$ to produce malic acid. A fumarate reductase gene (frdBC), a fumarase gene (fumB), a lactate dehydrogenase gene (ldhA) and an alcohol dehydrogenase gene (adhE) of the engineered strain of *E. coli* are knocked out, and a formate dehydrogenase (FDH), an acetyl coenzyme A synthetase (ACS), an acylated acetaldehyde dehydrogenase (ACDH), a formaldehyde lyase (FLS), a dihydroxyacetone kinase (DHAP), a malic enzyme (ME) and a phosphite oxidoreductase (PTXD) are overexpressed.

In an embodiment of the disclosure, a nucleotide sequence of the fumarate reductase gene is the same as a gene sequence of Gene ID: 948666 (SEQ ID NO. 7) or Gene ID: 948680 (SEQ ID NO. 8) on NCBI.

In an embodiment of the disclosure, a nucleotide sequence of the fumarase gene is the same as a gene sequence of Gene ID: 948642 (SEQ ID NO. 9) on NCBI.

In an embodiment of the disclosure, a nucleotide sequence of the lactate dehydrogenase gene is the same as a gene sequence of Gene ID: 946315 (SEQ ID NO. 10) on NCBI.

In an embodiment of the disclosure, a nucleotide sequence of the alcohol dehydrogenase gene is the same as a gene sequence of Gene ID: 945837 (SEQ ID NO. 11) on NCBI.

In an embodiment of the disclosure, the engineered strain of *E. coli* is obtained by using *Escherichia coli* MG1655 as a host; *Escherichia coli* MG1655 (ATCC® 700926™) is wild-type *E. coli* purchased on ATCC.

In an embodiment of the disclosure, a nucleotide sequence of a formate dehydrogenase gene is the same as a gene sequence of GenBank: ADK13769.1 (SEQ ID NO. 12) on NCBI.

In an embodiment of the disclosure, a nucleotide sequence of an acetyl coenzyme A synthetase gene is the same as a gene sequence of Gene ID: 948572 (SEQ ID NO. 13) on NCBI.

In an embodiment of the disclosure, a gene sequence of the acylated acetaldehyde dehydrogenase is shown in SEQ ID NO. 1.

In an embodiment of the disclosure, a gene sequence of the formaldehyde lyase is shown in SEQ ID NO. 2.

In an embodiment of the disclosure, a gene sequence of the dihydroxyacetone kinase is shown in SEQ ID NO. 3.

In an embodiment of the disclosure, a nucleotide sequence of a malic enzyme gene is the same as a gene sequence of Gene ID: 44998094 (SEQ ID NO. 14) on NCBI.

In an embodiment of the disclosure, a nucleotide sequence of a phosphite oxidoreductase gene is shown in SEQ ID NO. 4.

In an embodiment of the disclosure, the formate dehydrogenase, the acetyl coenzyme A synthetase, the acylated acetaldehyde dehydrogenase, the formaldehyde lyase and the dihydroxyacetone kinase are gradually ligated to a vector pER by isocaudamer assembly for overexpression, and a finally obtained plasmid is named pER-CF5A. The malic enzyme gene and the phosphite oxidoreductase gene are ligated to a vector pCDR by isocaudamer assembly for overexpression, and a finally obtained plasmid is named pCDR-ME-PTXD.

A second objective of the disclosure is to provide application of the engineered strain of E. coli in production of malic acid by fermentation. In an embodiment of the disclosure, the application includes that the engineered strain of E. coli is activated and then subjected to aerobic culture for 12-18 hours at a temperature of 30-37° C. and a rotation speed of 700-800 rpm under an oxygen ventilation rate of 0.8-1.2 vvm and pH of 6.5-7.0; then, the oxygen ventilation rate is adjusted to 0 vvm, the rotation speed is adjusted to 180-200 rpm, nitrogen is introduced at a speed of 1 vvm for 10-20 minutes, and the engineered strain is fermented for 60-80 hours under anaerobic conditions and neutral pH. Optionally, the application includes that the engineered strain of E. coli is activated and then subjected to aerobic culture at a temperature of 37° C. and a rotation speed of 800 rpm under an oxygen ventilation rate of 1 vvm and pH of 6.5-7.0; then, the oxygen ventilation rate is adjusted to 0 vvm, the rotation speed is adjusted to 200 rpm, nitrogen is introduced at a speed of 1 vvm for 10-20 minutes, and the engineered strain is fermented for 72 hours under anaerobic conditions with 250 g/L of $KHCO_3$ as an acid-base neutralizer to maintain pH=7.

A fermentation culture medium for fermentation contains 40-50 g/L of glucose, 20-50 mM of $Na_2HPO_3.5H_2O$, 30-50 mM of $KHCO_3$, 15.11 g/L of $Na_2HPO_4.12H_2O$, 3 g/L of $KH_2PO_4$, 1 g/L of $NH_4Cl$ and 0.5 g/L of NaCl, and 1 L of the culture medium contains 1 mL of a trace element solution; the trace element solution is prepared by dissolving 2.4 g/L of $FeCl_3.6H_2O$, 0.3 g/L of $CoCl_2.6H_2O$, 0.15 g/L of $CuCl_2$, 0.3 g/L of $ZnCl_2.4H_2O$, 0.3 g/L of $NaMnO_4$, 0.075 g/L of $H_3BO_3$ and 0.495 g/L of $MnCl_2.4H_2O$ in 0.1 M HCl.

In the disclosure, the engineered strain capable of reducing accumulation of malic acid is constructed by knocking out the fumarate reductase gene and the fumarase gene. Synthesis of malic acid by blocking a pyruvic acid as a node is one of shortest paths found so far, and when this path is constructed, synthesis pathways of main byproducts of the pyruvic acid node need to be blocked. In the disclosure, a purpose of increasing accumulation of a precursor pyruvic acid is achieved by knocking out the lactate dehydrogenase gene and the alcohol dehydrogenase gene.

In the disclosure, Escherichia coli MG1655 is used as an original strain, a metabolic engineering method is used, and the engineered strain of E. coli for producing malic acid is obtained by constructing a $CO_2$ fixation pathway, a malic acid synthesis pathway and blocking a malic acid metabolism pathway and a pyruvic acid metabolism branch. After fermentation for 72 hours, the yield of malic acid reaches 39 g/L, and the yield of glucose in malic acid is 1.53 mol/mol. The fermentation process is anaerobic fermentation, the product yield is high, and the production is high; at present, there is no report on production of malic acid by using a $CO_2$ fixation pathway in the disclosure.

According to the disclosure, $CO_2$ fixation is combined with production of malic acid so that not only can a new solution be provided for effectively alleviating the greenhouse effect, but also a new idea can be provided for production of malic acid at the same time, and waste substances are turned into useful substances.

DETAILED DESCRIPTION

Figure 1:
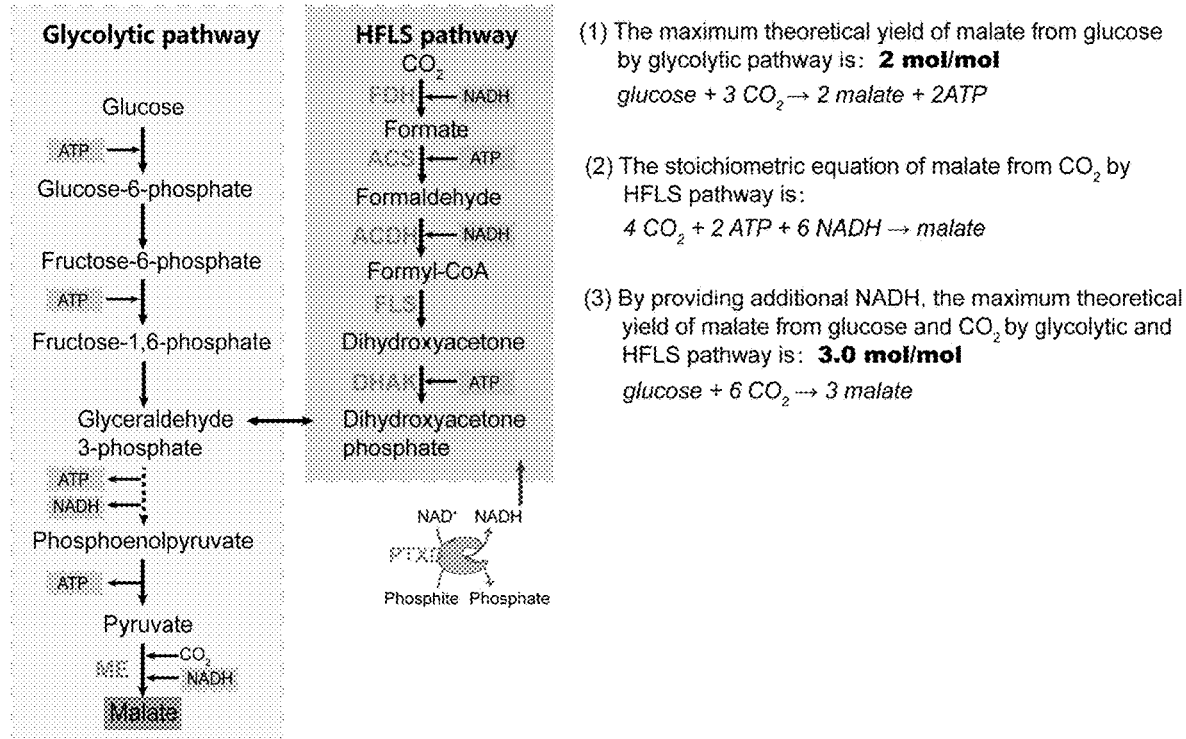
FIG. 1 shows construction of a synthetic path of malic acid by fixing $CO_2$ in an engineered strain of E. coli.

A detection method of malic acid (high performance liquid chromatography conditions): Aminex HPX-87H (7.8*300 mm) is used as a chromatographic column, a mobile phase includes 5 mM of $H_2SO_4$, the column temperature is 35° C., the detection wavelength is 210 nm, the injection volume is 10 μl, and the flow rate is 0.6 ml/min.

Purchase sources of commercial plasmid products: pKD4, pKD46 and pCP20 plasmids are purchased from BioVector NTCC. A pER plasmid is obtained by transforming a promoter region of pETM6 (purchased from addgene, #49795), and a pCDR plasmid is obtained by transforming a promoter region of pCDM4 (purchased from addgene, #49796).

Detection and calculation methods of a $CO_2$ fixation rate: (1) detection method: first, E. coli is cultured to a mid-log phase in an LB culture medium ($OD_{600}$ is 0.4-0.8); second, mid-log phase cells are collected and resuspended in 20 mL of an M9 culture medium (containing 5-10 g/L of glucose and 20-50 mM of $NaHCO_3$) until $OD_{600}$ is 3-5; then, 20 mL of a cell suspension is transferred into a 25 mL serum bottle and cultured for 2 hours; finally, concentrated hydrochloric acid is injected to release total inorganic carbon in the cell suspension, and the concentration of $CO_2$ in headspace gas of the serum bottle is detected by using a gas chromatograp. RTX-QBOND (30 m; inner diameter 0.32 mm, membrane thickness 10 mm, RESTEK, Pennsylvania, the United States) is used as a gas chromatographic column. Helium is used as a carrier gas, the chromatographic column is kept at a constant temperature of 80° C., the flow rate is 15 mL/min, and the injection port pressure is 68.8 kPa.

$$CO_2 \text{ fixation rate} = (B-A) \text{ mg/mL} * 5 \text{ mL}/(C \text{ mg}*2 \text{ h})$$

(2) Calculation method:

Note: A and B respectively refer to the concentration of $CO_2$ in the headspace of the serum bottle before and after culture, the headspace volume is 5 mL, the dry cell weight in the serum bottle is C mg, and the culture time is 2 hours.

Example 1: Construction of an Engineered Strain of E. coli Capable of Fixing $CO_2$ to Produce Malic Acid (1) Knockout of a Fumarate Reductase Gene frdBC in E. coli MG1655

According to an frdBC gene sequence of *Escherichia coli* MG1655 in an NCBI database, primers QCfrdBC-S and QCfrdBC-A were designed and knocked out (Table 1), a pKD4 plasmid was used as a template for amplifying an frdBC knockout frame, and gel recovery was performed. Note: Two FRT sites (capable of being folded under the action of a flipase to remove a DNA sequence between the FRT sites) were contained in the pKD4 plasmid, and a coding gene, namely FRT-kan-FRT, of kanamycin (kan, as a gene knockout screening pressure) was located between the two FRT sites. When a gene was knocked out, a DNA fragment of FRT-kan-FRT was amplified by the designed primers. It should be pointed out that upstream and downstream 39-49 bp of the target gene were contained in the two designed amplification primers respectively, that is to say, the DNA fragment, which was called a knockout frame of the target gene, finally obtained was "upstream 39-49 bp of the target gene-FRT-kan-FRT-upstream 39-49 bp of the target gene". The frdBC knockout frame was transferred into competent cells containing a pKD46 plasmid of *E. coli* MG1655 by electrotransformation (the electrotransformation voltage and time were 1800 V and 5 ms respectively). The competent cells obtained after electrotransformation were coated on an LB solid culture medium plate containing kanamycin (50 g/mL) and subjected to inverted culture for 12-24 hours. After a single colony grew on the plate, positive transformants were screened by using verification primers YZfrdBC-S and YZfrdBC-A (Table 1).

Figure 2:
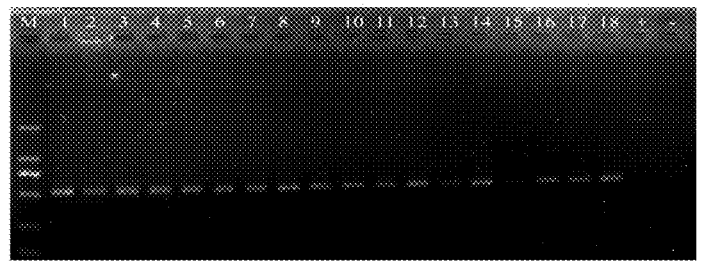
FIG. 2 is an frdBC gene knockout verification electrophoretogram [lanes 1-18 all refer to transformants in which an frdBC gene is successfully knocked out, lane 19 (marked "+") refers to colony PCR results of wild-type E. coli, and lane 19 (marked "−") refers to a no-treatment control group].

A pCP20 plasmid was transferred into the positive transformants to remove a kanamycin resistance gene, and then the primers YZfrdBC-S and YZfrdBC-A were used for verification; the electrophoretic band size of the transformants with successful knockedout was 529 bp, and the electrophoretic band size of a control group without knockout was 1917 bp (FIG. 2). A strain obtained after successfully knocking out the frdBC gene in MG1655 was named GH0101.

(2) Knockout of a Fumarase Gene fumB in E. coli GH0101

According to an fumB gene sequence of *Escherichia coli* MG1655 in the NCBI database, primers QCfumB-S and QCfumB-A were designed and knocked out (Table 1), a pKD4 plasmid was used as a template for amplifying an fumB knockout frame, and gel recovery was performed. The fumB knockout frame was transferred into competent cells containing a pKD46 plasmid of *E. coli* GH0101 by electrotransformation (the electrotransformation voltage and time were 1800 V and 5 ms respectively). The competent cells obtained after electrotransformation were coated on an LB solid culture medium plate containing kanamycin (50 g/mL) and subjected to inverted culture for 12-24 hours. After a single colony grew on the plate, positive transformants were screened by using verification primers YZfumB-S and YZfumB-A (Table 1).

Figure 3:
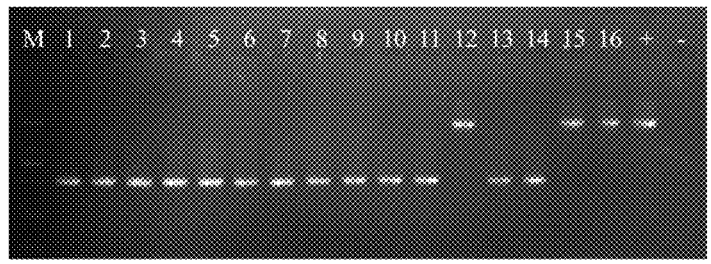
FIG. 3 is an fumB gene knockout verification electrophoretogram [lanes 1-11 and 13-14 all refer to transformants in which an fumB gene is successfully knocked out, lanes 12 and 15-16 are transformants in which the fumB gene is not successfully knocked out, lane 17 (marked "+") refers to colony PCR results of wild-type E. coli, and lane 18 (marked "−") refers to a no-treatment control group].

A pCP20 plasmid was transferred into the positive transformants to remove a kanamycin resistance gene, and then the primers YZfumB-S and YZfumB-A were used for verification; the electrophoretic band size of the transformants with successful knockedout was 506 bp, and the electrophoretic band size of a control group without knockout was 1940 bp (FIG. 3). A strain obtained after successfully knocking out the fumB gene in GH0101 was named GH0201.

(3) Knockout of a Lactate Dehydrogenase Gene ldhA in E. coli GH0201

According to an ldhA gene sequence of *Escherichia coli* MG1655 in the NCBI database, primers QCldhA-S and QCldhA-A were designed and knocked out (Table 1), a pKD4 plasmid was used as a template for amplifying an ldhA knockout frame, and gel recovery was performed. The ldhA knockout frame was transferred into competent cells containing a pKD46 plasmid of *E. coli* GH0201 by electrotransformation (the electrotransformation voltage and time were 1800 V and 5 ms respectively). The competent cells obtained after electrotransformation were coated on an LB solid culture medium plate containing kanamycin (50 g/mL) and subjected to inverted culture for 12-24 hours. After a single colony grew on the plate, positive transformants were screened by using verification primers YZldhA-S and YZldhA-A (Table 1).

Figure 4:
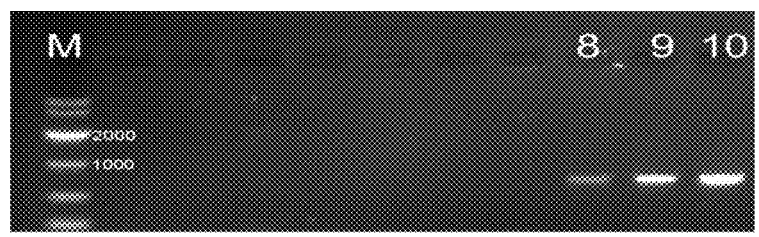
FIG. 4 is an ldhA gene knockout verification electrophoretogram [lane 3 is transformants in which an ldhA gene is not successfully knocked out, and lanes 8-10 refer to transformants in which the ldhA gene is successfully knocked out].

A pCP20 plasmid was transferred into the positive transformants to remove a kanamycin resistance gene, and then the primers YZldhA-S and YZldhA-A were used for verification; the electrophoretic band size of the transformants with successful knockedout was 744 bp, and the electrophoretic band size of a control group without knockout was 2132 bp (FIG. 4). A strain obtained after successfully knocking out the ldhA gene in GH0201 was named GH0301.

(4) Knockout of an Alcohol Dehydrogenase Gene adhE in E. coli GH0301

According to an adhE gene sequence of *Escherichia coli* MG1655 in the NCBI database, primers QCadhE-S and QCadhE-A were designed and knocked out (Table 1), a pKD4 plasmid was used as a template for amplifying an adhE knockout frame, and gel recovery was performed. The adhE knockout frame was transferred into competent cells containing a pKD46 plasmid of *E. coli* GH0301 by electrotransformation (the electrotransformation voltage and time were 1800 V and 5 ms respectively). The competent cells obtained after electrotransformation were coated on an LB solid culture medium plate containing kanamycin (50 g/mL) and subjected to inverted culture for 12-24 hours. After a single colony grew on the plate, positive transformants were screened by using verification primers YZadhE-S and YZadhE-A (Table 1).

Figure 5:
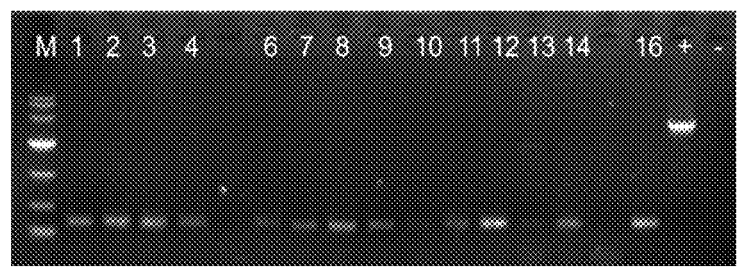
FIG. 5 is an adhE gene knockout verification electrophoretogram [lanes 1-4, 6-14 and 16 all refer to transformants in which an adhE gene is successfully knocked out, lane 17 (marked "+") refers to colony PCR results of wild-type E. coli, and lane 18 (marked "−") refers to a no-treatment control group].

A pCP20 plasmid was transferred into the positive transformants to remove a kanamycin resistance gene, and then the primers YZadhE-S and YZadhE-A were used for verification; the electrophoretic band size of the transformants with successful knockedout was 352 bp, and the electrophoretic band size of a control group without knockout was 2676 bp (FIG. 5). A strain obtained after successfully knocking out the adhE gene in GH0301 was named GH0401.

(5) Overexpression of FDH, ACS, ACDH, FLS and DHAK Proteins

According to a formate dehydrogenase gene sequence of *Clostridium ljungdahlii* provided in the NCBI database, amplification primers FDH-S and FDH-A were designed (Table 1), a genome of *C. ljungdahlii* was used as a template for amplifying a gene sequence of an FDH protein, and after gel recovery was performed, the gene sequence of the FDH protein was ligated to a plasmid pER (BglII and XhoI) by one-step homologous recombination to obtain a recombinant plasmid pER-FDH; a gene sequence of the pER plasmid was shown in SEQ ID NO. 5. According to an acetyl CoA synthetase gene sequence of *E. coli* MG1655 provided in the NCBI database, amplification primers ACS-S and ACS-A (Table 1) were designed, a genome of *E. coli* MG1655 was used as a template for amplifying a coding gene sequence of an ACS protein, and after gel recovery was performed, the coding gene sequence of the ACS protein was ligated to a plasmid pER (BglII and XhoI) by one-step homologous recombination to obtain a recombinant plasmid pER-ACS.

Figure 6:
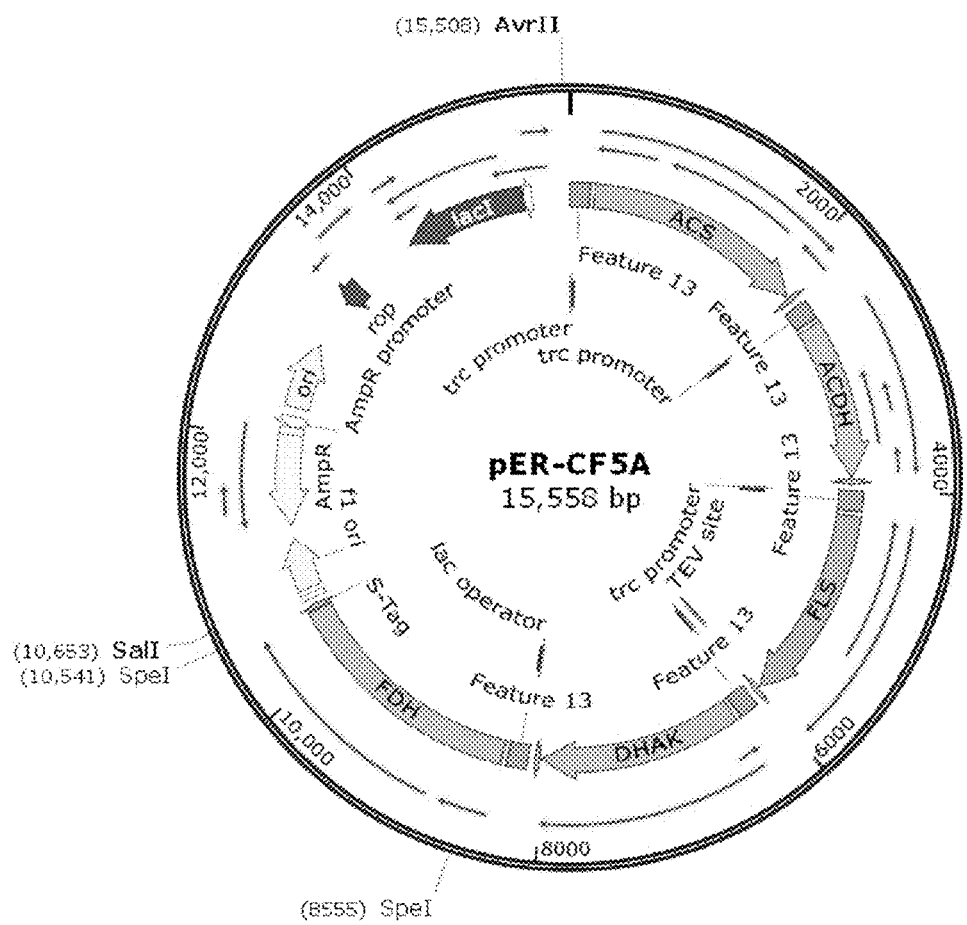
FIG. 6 is a diagram of a recombinant plasmid pER-CF5A.

According to ACDH, FLS and DHAK gene sequences provided in literatures, fragments of ACDH, FLS and DHAK encoding genes were separately obtained by gene synthesis and then ligated to a plasmid pER (BglII and XhoI) by enzyme digestion to obtain recombinant plasmids pER-ACDH, pER-FLS and pER-DHAK respectively; the five plasmids above (pER-FDH, pER-ACS, pER-ACDH, pER-FLS and pER-DHAK) were gradually assembled into a plasmid pER-CF5A by using an isocaudamer assembly technology [*ACS Synth Biol* 1, 256-266 (2012)]. BlnI and SpeI were used as isocaudamers, and enzyme digestion sites were shown in FIG. 6.

(6) Overexpression of ME and PTXD Proteins

Figure 7:
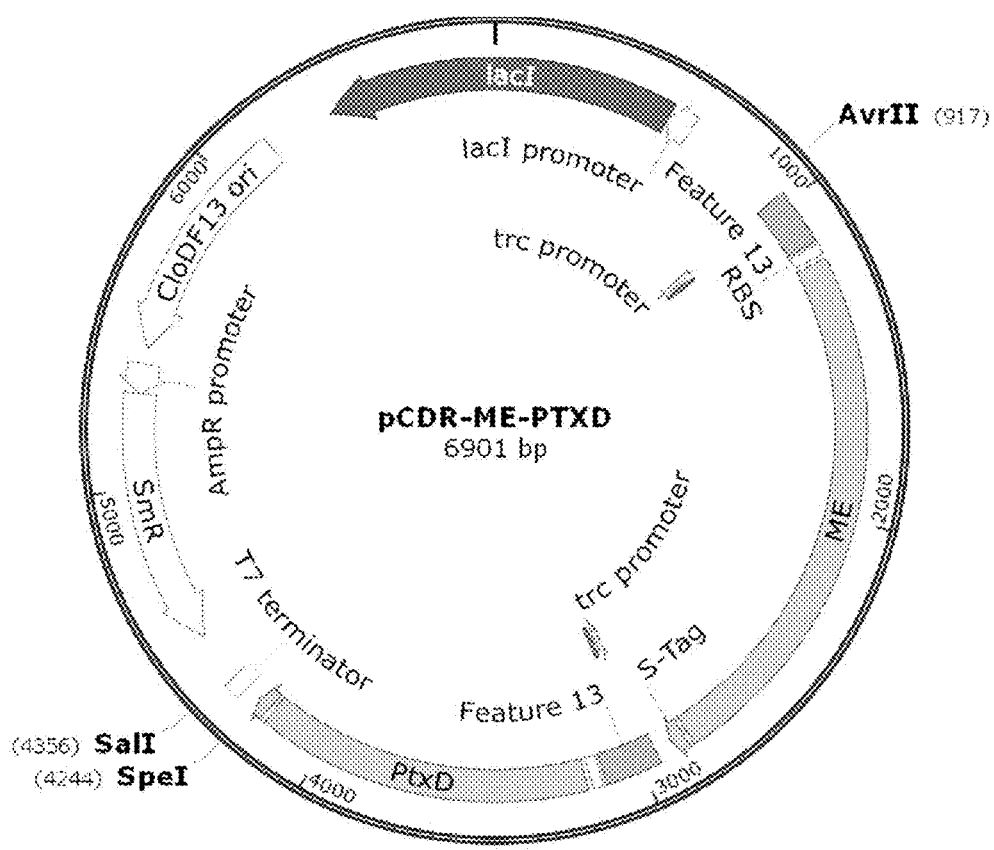
FIG. 7 is a diagram of a recombinant plasmid pCDR-ME-PTXD.

According to a malic enzyme gene sequence of *Clostridium acetobutylicum* provided in the NCBI database, amplification primers ME-S and ME-A were designed (Table 1), a genome of *Clostridium acetobutylicum* was used as a template for amplifying a gene fragment encoding a malic enzyme, and the gene fragment encoding the malic enzyme was ligated to a plasmid pCDR (BglII and XhoI) by one-step homologous recombination to obtain a recombinant plasmid pCDR-ME; a gene sequence of the pCDR plasmid was shown in SEQ ID NO. 6. Fragments of PTXD encoding genes were obtained by gene synthesis and then ligated to a plasmid pCDR (BglII and XhoI) by enzyme digestion to obtain a recombinant plasmid pCDR-PTXD; the two plasmids pCDR-ME and pCDR-PTXD were assembled into a plasmid pCDR-ME-PTXD by using the isocaudamer assembly technology. BlnI and SpeI were used as isocaudamers, and enzyme digestion sites were shown in FIG. 7.

The two plasmids pER-CF5A and pCDR-ME-PTXD obtained above were transferred into competent cells of *E. coli* GH0401 and coated on a double-resistant plate containing spectinomycin and ampicillin, and an obtained transformant was the genetically engineered strain of *E. coli* in the disclosure and named GH0407. In addition, a pER empty plasmid and pCDR-ME-PTXD were transferred into competent cells of *E. coli* GH0401 to obtain an engineered strain GH0402 as a control strain, so as to verify the effect of a heterologous $CO_2$ fixation pathway (HFLS, FIG. 1) on synthesis of malic acid.

Example 2 Production of Malic Acid by Fermentation of Engineered *E. coli* GH0402 and GH0407

A plate activation culture medium and activation culture conditions: An LB culture medium was used as the plate activation culture medium, and inverted culture in an incubator at 37° C. for 12 hours was used as an activation condition. A fermentation culture medium for fermentation contained 50 g/L of glucose, 20 mM of $Na_2HPO_3.5H_2O$, 50 mM of $KHCO_3$, 15.11 g/L of $Na_2HPO_4.12H_2O$, 3 g/L of $KH_2PO_4$, 1 g/L of $NH_4Cl$, 0.5 g/L of NaCl and 1 mL of a trace element solution; the trace element solution contained 2.4 g/L of $FeCl_3.6H_2O$, 0.3 g/L of $CoCl_2.6H_2O$, 0.15 g/L of $CuCl_2$, 0.3 g/L of $ZnCl_2.4H_2O$, 0.3 g/L of $NaMnO_4$, 0.075 g/L of $H_3BO_3$ and 0.495 g/L of $MnCl_2.4H_2O$, and 0.1M HCl was used as a solvent. After the engineered *E. coli* GH0402 and GH0407 were activated on the plate, a single colony was picked and added into a liquid LB seed culture medium and cultured at 37° C. and 200 rpm for 12 hours ($OD_{600}$ is 3-4). After seed culture was completed, the single colony was inoculated into the fermentation culture medium according to an inoculation amount of 2% (v/v) and cultured for 16 hours at a temperature of 37° C. and a rotation speed of 800 rpm under an oxygen ventilation rate of 1 vvm and pH of 7.0, oxygen ventilation was closed, nitrogen was introduced for 10-20 minutes (nitrogen ventilation rate: 1 vvm) to remove residual oxygen, and the single colony was continuously fermented for 72 hours under anaerobic conditions. 250 g/L of $KHCO_3$ was used as an acid-base neutralizer to maintain pH=7 in the whole process.

Figure 8:
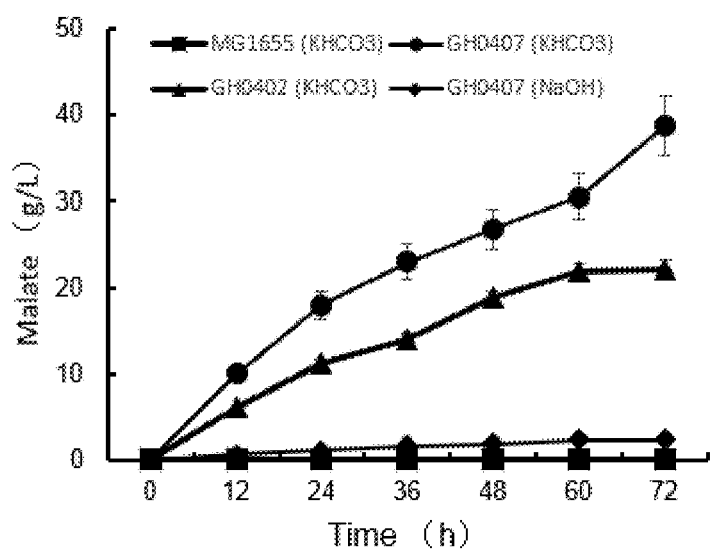
FIG. 8 shows a production-time curve of malic acid produced by fermentation of E. coli.
Figure 9:
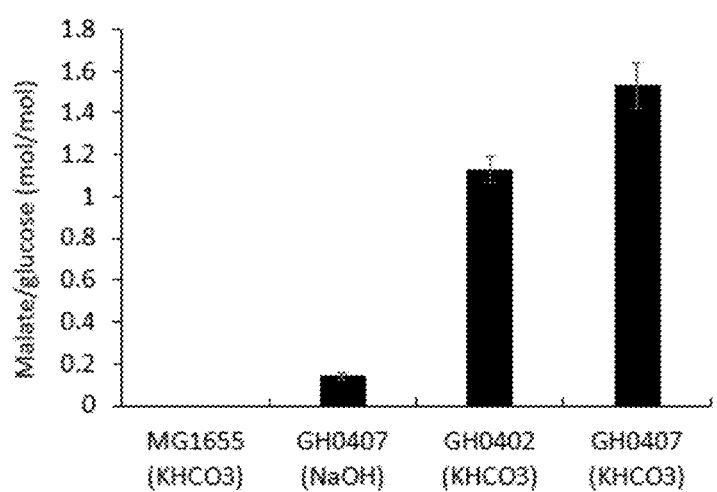
FIG. 9 shows the yield of malic acid produced by fermentation of E. coli.

It is detected by high performance liquid chromatography (HPLC) that the final yield of malic acid in a fermentation supernatant of GH0407 is 39 g/L (FIG. 8), the yield of glucose in malic acid reaches 1.53 mol/mol (the highest reported so far) (FIG. 9), and the $CO_2$ fixation rate of the engineered strain GH0407 is 41 mg $gDCW^{-1}$ $h^{-1}$ and is higher than that of most autotrophic blue-green algae (6-25 mg $gDCW^{-1}$ $h^{-1}$) (Table 2). $HCO_3^-$ and $CO_2$ in the fermentation solution can undergo a rapid reversible reaction, and at the same time, $HCO_3^-$ can also be used as an acid-base neutralizer to control the pH of the fermentation solution; therefore, a $CO_2$ environment can be created by adding $KHCO_3$ into the culture medium.

Two control groups are set: (i) $KHCO_3$ is not added into the fermentation solution, and NaOH is used as an acid-base neutralizer; (ii) the strain GH0402 without a $CO_2$ fixation pathway (namely, without a pER-CF5A plasmid) is used as a control group. It is shown through results that when NaOH is used as the acid-base neutralizer to replace $KHCO_3$ (that is to say, when a $CO_2$ environment is not provided), the yield of malic acid by using the engineered strain GH0407 is only 2.3 g/L, and the yield of glucose is only 0.14 mol/mol; the final yield of malic acid in a fermentation supernatant of the control group GH0402 is 22 g/L, and the yield of glucose is 1.13 mol/mol. It can be seen from data of the control group that the production and yield of malic acid are increased by $CO_2$.

TABLE 1

Sequences of gene knockout primers and protein overexpression primers

| Primer name | Number | Primer sequence |
|---|---|---|
| QCfrdBC-S | SEQ ID NO. 15 | ATGGCTGAGATGAAAAACCTGAAAATTGAGGTGGTGCGCTATAACCCG GGTGTAGGCTGGAGCTGCTTC |
| QCfrdBC-A | SEQ ID NO. 16 | TTACCAGTACAGGGCAACAAACAGGATTACGATGGTGGCAACCACAGT TATGGGAATTAGCCATGGTCC |

TABLE 1-continued

Sequences of gene knockout primers and protein overexpression primers

| Primer name | Number | Primer sequence |
|---|---|---|
| YZfrdBC-S | SEQ ID NO. 17 | TGGAGTACAGCGACGTGAAG |
| YZfrdBC-A | SEQ ID NO. 18 | GGAATACGCGACCAATGAAG |
| QCfumB-S | SEQ ID NO. 19 | ATGTCAAACAAACCCTTTATCTACCAGGCACCTTTCCCGATGGGGAAAGGTGTAGGCTGGAGCTGCTTC |
| QCfumB-A | SEQ ID NO. 20 | TTACTTAGTGCAGTTCGCGCACTGTTTGTTGACGATTTGCTGGAAGAAGATGGGAATTAGCCATGGTCC |
| YZfumB-S | SEQ ID NO. 21 | TGTGAGCGTATCGTGCGTC |
| YZfumB-A | SEQ ID NO. 22 | CGTGAAATTACAATCGCAAAC |
| QCldhA-S | SEQ ID NO. 23 | ATGAAACTCGCCGTTTATAGCACAAAACAGTACGACAAGAAGTACCTGCGTGTAGGCTGGAGCTGCTTC |
| QCldhA-A | SEQ ID NO. 24 | TTAAACCAGTTCGTTCGGGCAGGTTTCGCCTTTTTCCAGATTGCTTAAGATGGGAATTAGCCATGGTCC |
| YZldhA-S | SEQ ID NO. 25 | AACCCACAGCCCGAGCGT |
| YZldhA-A | SEQ ID NO. 26 | GGCTTACCGTTTACGCTTTCC |
| QCadhE-S | SEQ ID NO. 27 | ATGGCTGTTACTAATGTCGCTGAACTTAACGCACTCGTAGAGCGTGTAAGTGTAGGCTGGAGCTGCTTC |
| QCadhE-A | SEQ ID NO. 28 | TTAAGCGGATTTTTTCGCTTTTTTCTCAGCTTTAGCCGGAGCAGCTTCTATGGGAATTAGCCATGGTCC |
| YZadhE-S | SEQ ID NO. 29 | TCATCACCGCACTGACTAT |
| YZadhE-A | SEQ ID NO. 30 | TCCTTAACTGATCGGCATT |
| FDH-S | SEQ ID NO. 31 | agatatacatatggcagatctGATGAAAAGTATACTAACTACTTGTCCTTATTGT |
| FDH-A | SEQ ID NO. 32 | ggtttctttaccagactcgagTTAAGCGTCTTTACGCATACTCTTTT |
| ACS-S | SEQ ID NO. 33 | agatatacatatggcagatctGATGAGCCAAATTCACAAACACACC |
| ACS-A | SEQ ID NO. 34 | ggtttctttaccagactcgagTTACGATGGCATCGCGATAGC |
| ME-S | SEQ ID NO. 35 | agatatacatatggcagatctGATGAATAATTTAAAAGGTTTAGAATTACTAAGAA |
| ME-A | SEQ ID NO. 36 | ggtttctttaccagactcgagTTATCTATAGTATGGTTCCCAAATTTCA |

TABLE 2

Comparison of $CO_2$ fixation rate of microorganisms

| Strain name | $CO_2$ fixation rate | Culture conditions | References |
|---|---|---|---|
| *Botryococcus braunii* SAG-30.81 | 6.8 mg gDCW$^{-1}$ h$^{-1}$ | 11 L fermentation tank | Bioresour Technol 101, 5892-5896 (2010) |
| *Chlorella vulgaris* | 9.3 mg gDCW$^{-1}$ h$^{-1}$ | Photoreactor | Int J Greenh Gas Con 14, 169-176 (2013) |
| *Phaeodactylum tricornutum* | 23.7 mg gDCW$^{-1}$ h$^{-1}$ | Photoreactor | Biotechnol Bioeng 67, 465-475 (2000) |
| *E. coli* JB | 0.95 mg gDCW$^{-1}$ h$^{-1}$ | 3 L fermentation tank | Bioresour Technol 150, 79-88 (2013) |
| *E. coli* | 41 mg gDCW$^{-1}$ h$^{-1}$ | 3.6 L fermentation tank | The disclosure |

What is claimed is:

1. An engineered strain of *E. coli* for producing malic acid by fixing $CO_2$, wherein a fumarate reductase gene (frdBC), a fumarase gene (fumB), a lactate dehydrogenase gene (ldhA) and an alcohol dehydrogenase gene (adhE) of the engineered strain of *E. coli* are knocked out, and a formate dehydrogenase (FDH), an acetyl coenzyme A synthetase (ACS), an acylated acetaldehyde dehydrogenase (ACDH), a formaldehyde lyase (FLS), a dihydroxyacetone kinase (DHAK), a malic enzyme (ME) and a phosphite oxidoreductase (PTXD) are overexpressed; wherein the formate dehydrogenase, the acetyl coenzyme A synthetase, the acylated acetaldehyde dehydrogenase, the formaldehyde lyase and the dihydroxyacetone kinase are gradually ligated to a vector by isocaudamer assembly for overexpression; wherein the engineered strain of *E. coli* is obtained by using *Escherichia coli* MG1655 as a host; wherein a malic enzyme gene and a phosphite oxidoreductase gene are ligated to the vector by isocaudamer assembly for overexpression; wherein the nucleotide sequence of the vector is set forth in SEQ ID NO: 6.

2. The engineered strain of *E. coli* for producing malic acid by fixing $CO_2$ according to claim 1, wherein a nucleotide sequence of the fumarate reductase gene is set forth in SEQ ID NO:7 or SEQ ID NO:8, a nucleotide sequence of the fumarase gene is set forth in SEQ ID NO:9, a nucleotide sequence of the lactate dehydrogenase gene is set forth in SEQ ID NO:10, a nucleotide sequence of the alcohol dehydrogenase gene is set forth in SEQ ID NO:11, a nucleotide sequence of a formate dehydrogenase gene is set forth in SEQ ID NO:12, a nucleotide sequence of an acetyl coenzyme A synthetase gene is set forth in SEQ ID NO:13, a gene sequence of the acylated acetaldehyde dehydrogenase is set forth in SEQ ID NO:1, a gene sequence of the formaldehyde lyase is set forth in SEQ ID NO:2, a gene sequence of the dihydroxyacetone kinase is set forth in SEQ ID NO:3, a nucleotide sequence of the malic enzyme gene is set forth in SEQ ID NO:14, and a nucleotide sequence of the phosphite oxidoreductase gene is set forth in SEQ ID NO:4.

3. A method for producing malic acid, comprising fermenting the engineered strain of *E. coli* according to claim 2 in a fermentation culture system comprising glucose.

4. The method according to claim 3, wherein a fermentation culture medium for fermentation comprises 40-50 g/L of glucose, 20-50 mM of $Na_2HPO_3 \cdot 5H_2O$, 30-50 mM of $KHCO_3$, 15.11 g/L of $Na_2HPO_4 \cdot 12H_2O$, 3 g/L of $KH_2PO_4$, 1 g/L of $NH_4Cl$ and 0.5 g/L of NaCl, and 1 L of the culture medium contains 1 mL of a trace element solution; the trace element solution is prepared by dissolving 2.4 g/L of $FeCl_3 \cdot 6H_2O$, 0.3 g/L of $CoCl_2 \cdot 6H_2O$, 0.15 g/L of $CuCl_2$, 0.3 g/L of $ZnCl_2 \cdot 4H_2O$, 0.3 g/L of $NaMnO_4$, 0.075 g/L of $H_3BO_3$ and 0.495 g/L of $MnCl_2 \cdot 4H_2O$ in 0.1 M HCl.

5. The method according to claim 3, wherein fermentation is performed at 30-37° C. for lasting at least 24 hours.

6. The method according to claim 5, wherein pH is controlled to be 6.5-7.0 in a fermentation process.

7. The method according to claim 3, wherein the engineered strain of *E. coli* is activated and then subjected to aerobic culture for 12-18 hours at a temperature of 30-37° C. and a rotation speed of 700-800 rpm under an oxygen ventilation rate of 0.8-1.2 vvm and pH of 6.5-7.0; then, the oxygen ventilation rate is adjusted to 0 vvm, the rotation speed is adjusted to 180-200 rpm, nitrogen is introduced at a speed of 1 vvm for 10-20 minutes, and the engineered strain of *E. coli* is fermented for 60-80 hours under anaerobic conditions and neutral pH.

8. The method according to claim 7, wherein the fermentation culture medium for fermentation comprises 40-50 g/L of glucose, 20-50 mM of $Na_2HPO_3 \cdot 5H_2O$, 30-50 mM of $KHCO_3$, 15.11 g/L of $Na_2HPO_4 \cdot 12H_2O$, 3 g/L of $KH_2PO_4$, 1 g/L of $NH_4Cl$ and 0.5 g/L of NaCl, and 1 L of the culture medium contains 1 mL of the trace element solution; the trace element solution is prepared by dissolving 2.4 g/L of $FeCl_3 \cdot 6H_2O$, 0.3 g/L of $CoCl_2 \cdot 6H_2O$, 0.15 g/L of $CuCl_2$, 0.3 g/L of $ZnCl_2 \cdot 4H_2O$, 0.3 g/L of $NaMnO_4$, 0.075 g/L of $H_3BO_3$ and 0.495 g/L of $MnCl_2 \cdot 4H_2O$ in 0.1 M HCl.

* * * * *

SEQUENCE LISTING

<160> NUMBER OF SEQ ID NOS: 36

<210> SEQ ID NO 1
<211> LENGTH: 1383
<212> TYPE: DNA
<213> ORGANISM: Artificial sequence
<220> FEATURE:
<223> OTHER INFORMATION: Synthetic DNA

<400> SEQUENCE: 1

```
atgagcctgg aagataagga cctgcgtagc atccaagaag tgcgtaacct gatcgaatct      60
gcgaataagg cccaaaaaga actggcggcg atgtcacagc aacagattga taccatcgtg     120
aaagcgattg ccgacgcagg ctatggtgcg cgtgaaaaac tggctaagat ggcgcacgaa     180
gaaacgggct ttggtatttg caggataaaa gttatcaaga acgtcttcgc ctcgaagcat     240
gtctacaact acatcaagga tatgaagacc atcggtatgc tgaaagaaga caacgaaaag     300
aaagttatgg aagtcgcagt gccgctgggc gtggttgctg gtctgattcc gtcaaccaat     360
ccgacctcga cggtgatcta caaaacgctg atttcaatca aggcgggcaa cagtatcgtg     420
tttagcccgc acccgaatgc cctgaaagca attctgaaaa ccgtccgcat tatctcagaa     480
gcggccgaaa aagcaggctg cccgaagggt gctatttcgt gtatgaccgt tccgacgatc     540
caaggcaccg atcagctgat gaaacataag gacaccgctg tcattctggc aacgggcggt     600
tctgcgatgg tgaaagcagc ttatagctct ggcaccccgg caattggtgt gggtccgggc     660
aacggtccgg cctttattga acgtagtgcg aatatcccgc gtgcggttaa acacatcctg     720
gattccaaga ccttcgacaa cggtacgatt tgcgccagcg aacagtctgt cgtggttgaa     780
cgtgtcaata aagaagctgt gatcgcggaa tttcgcaagc aaggcgcaca cttcctgagt     840
gatgctgaag cggtgcagct gggcaaattc attctgcgtc gaacggtag catgaatccg     900
gcgattgtgg caaaagcgt gcaacatatc gcaaacctgg caggtctgac cgtgccggcc     960
gatgcacgtg ttctgattgc ggaagaaacg aaagttggcg ccaagatccc gtatagtcgc    1020
gaaaaactgg ccccgattct ggcattttac accgctgaaa cgtggcagga agcatgcgaa    1080
ctgagcatgg atattctgta ccatgaaggc gctggtcaca ccctgattat ccatagcgaa    1140
gacaaagaaa ttatccgtga atttgcactg aaaaagccgg tttctcgcct gctggtcaac    1200
acgccgggcg cgctgggcgg cattggtgcc accacgaatc tggttccggc actgacgctg    1260
ggctgtggtg ctgtcggcgg tagttcctca tcggataata tcggtccgga aaacctgttt    1320
aatattcgtc gcatcgccac cggcgtgctg gaactggaag acattcgcga aggcggtagc    1380
taa                                                                  1383
```

<210> SEQ ID NO 2
<211> LENGTH: 1728
<212> TYPE: DNA
<213> ORGANISM: Artificial sequence
<220> FEATURE:
<223> OTHER INFORMATION: Synthetic DNA

<400> SEQUENCE: 2

```
atggctatga ttactggtgg tgaactggtt gttcgtaccc tgattaaagc tggcgtagaa      60
catctgtttg gcctgcatgg cattcatatt gacaccattt tccaggcttg cctggaccac     120
gacgtcccaa tcattgatac tcgccacgaa gcggcggcag ccacgctgc ggaaggttat     180
gcccgcgcgg cgctaaaact gggtgttgcc ctggtgaccg ctggcggtgg ctttaccaat     240
gccgttacgc cgatcgcgaa cgctcggacc gatcgcactc cggttctgtt cctgaccggt     300
```

```
tctggtgctc ttcgtgatga cgaaaccaac accctgcagg ccggtattga tcaggtggcc      360
atggcggccc cgatcacgaa atgggctcat cgtgttatgg caactgaaca catcccgcgt      420
ctggttatgc aggccattcg tgccgctctg agcgccccac gtggcccggt gctgctggat      480
ctgccatggg acatcctgat gaaccaaatc gatgaagatt ccgttatcat cccagacctg      540
gtgctgtctg ctcacggtgc ccatccagac ccggctgacc tggaccaggc tctggcactg      600
ctgcgtaaag ccgaacgccc agttatcgta ctgggctccg aggcgtcccg caccgcacgc      660
aagaccgcac tgagcgcatt cgtagcggcg accggtgtac cggttttcgc tgactatgaa      720
ggcctgtcca tgctgagcgg cctgccggac gctatgcgtg gcggcctggt gcagaacctg      780
tactcctttg caaaagctga tgcagctccg gacctggtac tgatgctggg tgctcgtttc      840
ggtctgaaca ccggtcatgg ttccggtcaa ctgatcccgc attctgctca ggtgatccag      900
gtggatccag acgcgtgtga actgggtcgc ctgcaaggca tcgcgctggg tatcgtggct      960
gatgtaggtg gcaccattga agcgctggct caggcgaccg cacaggacgc cgcgtggccg     1020
gaccgcggcg actggtgcgc caaggtaact gacctggccc aggagcgtta cgcttccatc     1080
gcggctaaat ccagctctga acatgcgctg cacccgttcc acgcttctca ggttatcgcg     1140
aaacacgtgg acgcaggcgt gaccgtcgtt gcggatggtg gcctgactta tctgtggctg     1200
tccgaagtta tgtctcgtgt caaaccaggc ggcttcctgt gccacggcta tctgaacagc     1260
atgggtgtag gcttcggtac tgccctgggt gcgcaggttg cggatctgga ggcaggtcgt     1320
cgtaccatcc tggtgaccgg cgacggctct gttggttatt ccattggcga attcgacacc     1380
ctggtacgca aacagctgcc gctgattgta attatcatga caaccagtc ttggggctgg     1440
accctgcact ttcagcagct ggccgttggt cctaaccgtg tcaccggcac ccgcctggaa     1500
aatggttcct atcacggcgt tgctgcggca ttcggtgctg atggttacca cgtcgactct     1560
gtcgagagct tcagcgccgc tctggctcag gcactggcac acaaccgccc ggcatgcatc     1620
aacgttgctg tggccctgga cccgatcccg ccggaggaac tgatcctgat tggcatggac     1680
ccgtttgcgg gctccacgga gaatctgtat ttccaatccg gcgcgtaa                  1728
```

<210> SEQ ID NO 3
<211> LENGTH: 1755
<212> TYPE: DNA
<213> ORGANISM: Artificial sequence
<220> FEATURE:
<223> OTHER INFORMATION: Synthetic DNA

<400> SEQUENCE: 3

```
atgtccgcta aatcgtttga agtcacagat ccagtcaatt caagtctcaa agggtttgcc      60
cttgctaacc cctccattac gctggtccct gaagaaaaaa ttctcttcag aaagaccgat     120
tccgacaaga tcgcattaat ttctggtggt ggtagtggac atgaacctac acacgccggt     180
ttcattggta agggtatgtt gagtggcgcc gtggttggcg aaatttttgc atccccttca     240
acaaaacaga ttttaaatgc aatccgttta gtcaatgaaa atgcgtctgg cgttttattg     300
attgtgaaga actacacagg tgatgttttg cattttggtc tgtccgctga gagagcaaga     360
gccttgggta ttaactgccg cgttgctgtc ataggtgatg atgttgcagt ggcagagaa      420
aagggtggta tggttggtag aagagcattg gcaggtaccg ttttggttca taagattgta     480
ggtgccttcg cagaagaata ttctagtaag tatggcttag acggtacagc taaagtggct     540
aaaattatca acgacaattt ggtgaccatt ggatcttctt tagaccattg taaagttcct     600
```

-continued

| | |
|---|---|
| ggcaggaaat tcgaaagtga attaaacgaa aaacaaatgg aattgggtat gggtattcat | 660 |
| aacgaacctg gtgtgaaagt tttagaccct attccttcta ccgaagactt gatctccaag | 720 |
| tatatgctac caaaactatt ggatccaaac gataaggata gagcttttgt aaagtttgat | 780 |
| gaagatgatg aagttgtctt gttagttaac aatctcggcg gtgtttctaa ttttgttatt | 840 |
| agttctatca cttccaaaac tacggatttc ttaaaggaaa attacaacat aaccccggtt | 900 |
| caaacaattg ctggcacatt gatgacctcc ttcaatggta atgggttcag tatcacatta | 960 |
| ctaaacgcca ctaaggctac aaaggctttg caatctgatt tgaggagat caaatcagta | 1020 |
| ctagacttgt tgaacgcatt tacgaacgca ccgggctggc caattgcaga ttttgaaaag | 1080 |
| acttctgccc catctgttaa cgatgacttg ttacataatg aagtaacagc aaaggccgtc | 1140 |
| ggtacctatg actttgacaa gtttgctgag tggatgaaga gtggtgctga acaagttatc | 1200 |
| aagagcgaac cgcacattac ggaactagac aatcaagttg gtgatggtga ttgtggttac | 1260 |
| actttagtgg caggagttaa aggcatcacc gaaaaccttg acaagctgtc gaaggactca | 1320 |
| ttatctcagg cggttgccca aatttcagat ttcattgaag gctcaatggg aggtacttct | 1380 |
| ggtggtttat attctattct tttgtcgggt ttttcacacg gattaattca ggtttgtaaa | 1440 |
| tcaaaggatg aacccgtcac taaggaaatt gtggctaagt cactcggaat tgcattggat | 1500 |
| actttataca aatatacaaa ggcaaggaag ggatcatcca ccatgattga tgctttagaa | 1560 |
| ccattcgtta agaatttac tgcatctaag gatttcaata aggcggtaaa agctgcagag | 1620 |
| gaaggtgcta atccactgc tacattcgag gccaaatttg gcagagcttc gtatgtcggc | 1680 |
| gattcatctc aagtagaaga tcctggtgca gtaggcctat gtgagttttt gaaggggggtt | 1740 |
| caaagcgcct tgtaa | 1755 |

<210> SEQ ID NO 4
<211> LENGTH: 1011
<212> TYPE: DNA
<213> ORGANISM: Artificial sequence
<220> FEATURE:
<223> OTHER INFORMATION: Synthetic DNA

<400> SEQUENCE: 4

| | |
|---|---|
| atgctgccga aactggtgat cacgcatcgc gtgcacgacg aaattctcca gctcctcgcg | 60 |
| ccacattgcg aactgatgac gaaccagacc gatagcacgc tgaccgcga agaaattctg | 120 |
| cgtcgctgcc gtgatgcgca agcgatgatg gcctttatgc cggatcgcgt tgatgccgac | 180 |
| tttctgcaag cgtgcccaga actgcgtgtt gttggctgcg ccctcaaagg cttcgacaac | 240 |
| ttcgacgtgg atgcgtgcac ggcccgtggc gtttggctga cctttgtgcc ggatctgctg | 300 |
| accgttccga ccgcggaact ggcgattggt ctggccgtgg gtctcggtcg tcatctgcgt | 360 |
| gcggccgacg ccttcgttcg tagcggcgag ttccaaggct ggcagccgca gttctacggc | 420 |
| accggtctgg ataatgccac cgttggtatc ctcggcatgg gtgcgatcgg tctggcgatg | 480 |
| gcggatcgtc tgcaaggctg gggtgccacc ctccagtatc atgaagcgaa ggcgctggat | 540 |
| acgcaaaccg aacagcgcct cggtctgcgt caagttgcgt gcagcgagct gttcgccagt | 600 |
| agcgatttca ttctgctcgc gctgccgctc aacgcgata cccagcatct cgttaacgcc | 660 |
| gaactgctgg cgctggttcg tccgggcgcg ctgctggtga cccgtgccg tggtagtgtg | 720 |
| gttgatgaag ccgccgttct cgccgcgctg aacgtggtc aactgggcgg ttacgccgcc | 780 |
| gacgtttttg agatggaaga ttgggcgcgt gcggaccgtc cacgtctgat cgatccggcg | 840 |
| ctgctggccc atccaaacac gctgttcacg ccgcatatcg gtagtgccgt tcgtgccgtg | 900 |

-continued

| | |
|---|---|
| cgtctggaaa tcgaacgctg cgcggcgcag aatatcatcc aagttctcgc cggtgcccgc | 960 |
| ccaattaatg ccgccaatcg tctgccaaaa gccgaaccag cggcgtgcta a | 1011 |

<210> SEQ ID NO 5
<211> LENGTH: 5351
<212> TYPE: DNA
<213> ORGANISM: Artificial sequence
<220> FEATURE:
<223> OTHER INFORMATION: Synthetic DNA

<400> SEQUENCE: 5

| | |
|---|---|
| ttgacaatta atcatccggc tcgtataatg tgtggaattg tgagcggata acaatttcac | 60 |
| acaggaaaca gcgccgctga gaaaaagcga agcggcactg ctctttaaca atttatcaga | 120 |
| caatctgtgt gggcactcga ccggaattat cgattaactt tattattaaa aattacctct | 180 |
| agaaataatt ttgtttaact ttaagaagga gatatacata tggcagatct caattggata | 240 |
| tcggccggcc acgcgatcgc tgacgtcggt accctcgagt ctggtaaaga aaccgctgct | 300 |
| gcgaaatttg aacgccagca catggactcg tctactagtc gcagcttaat taacctaaac | 360 |
| tgctgccacc gctgagcaat aactagcata accccttggg gcctctaaac gggtcttgag | 420 |
| gggttttttg ctagcgaaag gaggagtcga ctatatccgg attggcgaat gggacgcgcc | 480 |
| ctgtagcggc gcattaagcg cggcgggtgt ggtggttacg cgcagcgtga ccgctacact | 540 |
| tgccagcgcc ctagcgcccg ctcctttcgc tttcttccct tcctttctcg ccacgttcgc | 600 |
| cggctttccc cgtcaagctc taaatcgggg gctcccttta gggttccgat ttagtgcttt | 660 |
| acggcacctc gaccccaaaa aacttgatta gggtgatggt tcacgtagtg gccatcgcc | 720 |
| ctgatagacg ttttttcgcc ctttgacgtt ggagtccacg ttctttaata gtggactctt | 780 |
| gttccaaact ggaacaacac tcaaccctat ctcggtctat tcttttgatt tataagggat | 840 |
| tttgccgatt tcggcctatt ggttaaaaaa tgagctgatt taacaaaaat ttaacgcgaa | 900 |
| ttttaacaaa atattaacgt ttacaatttc tggcggcacg atggcatgag attatcaaaa | 960 |
| aggatcttca cctagatcct tttaaattaa aaatgaagtt ttaaatcaat ctaaagtata | 1020 |
| tatgagtaaa cttggtctga cagttaccaa tgcttaatca gtgaggcacc tatctcagcg | 1080 |
| atctgtctat ttcgttcatc catagttgcc tgactccccg tcgtgtagat aactacgata | 1140 |
| cgggagggct taccatctgg ccccagtgct gcaatgatac cgcgagaccc acgctcaccg | 1200 |
| gctccagatt tatcagcaat aaaccagcca gccggaaggg ccgagcgcag aagtggtcct | 1260 |
| gcaactttat ccgcctccat ccagtctatt aattgttgcc gggaagctag agtaagtagt | 1320 |
| tcgccagtta atagtttgcg caacgttgtt gccattgcta caggcatcgt ggtgtcacgc | 1380 |
| tcgtcgtttg gtatggcttc attcagctcc ggttcccaac gatcaaggcg agttacatga | 1440 |
| tcccccatgt tgtgcaaaaa agcggttagc tccttcggtc ctccgatcgt tgtcagaagt | 1500 |
| aagttggccg cagtgttatc actcatggtt atggcagcac tgcataattc tcttactgtc | 1560 |
| atgccatccg taagatgctt ttctgtgact ggtgagtact caaccaagtc attctgagaa | 1620 |
| tagtgtatgc ggcgaccgag ttgctcttgc ccggcgtcaa tacgggataa taccgcgcca | 1680 |
| catagcagaa ctttaaaagt gctcatcatt ggaaaacgtt cttcggggcg aaaactctca | 1740 |
| aggatcttac cgctgttgag atccagttcg atgtaaccca ctcgtgcacc caactgatct | 1800 |
| tcagcatctt ttactttcac cagcgtttct gggtgagcaa aaacaggaag gcaaaatgcc | 1860 |
| gcaaaaaagg gaataagggc gacacggaaa tgttgaatac tcatactctt ccttttcaa | 1920 |

```
tcatgattga agcatttatc agggttattg tctcatgagc ggatacatat tgaatgtat       1980 ttagaaaaat aaacaaatag gtcatgacca aaatccctta acgtgagttt tcgttccact      2040
gagcgtcaga ccccgtagaa aagatcaaag gatcttcttg agatcctttt tttctgcgcg     2100
taatctgctg cttgcaaaca aaaaaaccac cgctaccagc ggtggtttgt ttgccggatc     2160
aagagctacc aactcttttt ccgaaggtaa ctggcttcag cagagcgcag ataccaaata    2220
ctgtccttct agtgtagccg tagttaggcc accacttcaa gaactctgta gcaccgccta    2280
catacctcgc tctgctaatc ctgttaccag tggctgctgc cagtggcgat aagtcgtgtc    2340
ttaccgggtt ggactcaaga cgatagttac cggataaggc gcagcggtcg ggctgaacgg    2400
ggggttcgtg cacacagccc agcttggagc gaacgaccta caccgaactg agatacctac    2460
agcgtgagct atgagaaagc gccacgcttc ccgaagggag aaaggcggac aggtatccgg    2520
taagcggcag ggtcggaaca ggagagcgca cgagggagct tccaggggga aacgcctggt    2580
atctttatag tcctgtcggg tttcgccacc tctgacttga gcgtcgattt ttgtgatgct    2640
cgtcaggggg gcggagccta tggaaaaacg ccagcaacgc ggcctttttta cggttcctgg    2700 ccttttgctg gccttttgct cacatgttct ttcctgcgtt atccctgat tctgtggata     2760 accgtattac cgcctttgag tgagctgata ccgctcgccg cagccgaacg accgagcgca    2820
gcgagtcagt gagcgaggaa gcggaagagc gcctgatgcg gtattttctc cttacgcatc    2880
tgtgcggtat ttcacaccgc atatatggtg cactctcagt acaatctgct ctgatgccgc    2940
atagttaagc cagtatacac tccgctatcg ctacgtgact gggtcatggc tgcgccccga    3000
cacccgccaa cacccgctga cgcgccctga cgggcttgtc tgctcccggc atccgcttac    3060
agacaagctg tgaccgtctc cgggagctgc atgtgtcaga ggttttcacc gtcatcaccg    3120
aaacgcgcga ggcagctgcg gtaaagctca tcagcgtggt cgtgaagcga ttcacagatg    3180
tctgcctgtt catccgcgtc cagctcgttg agtttctcca gaagcgttaa tgtctggctt    3240
ctgataaagc gggccatgtt aagggcggtt ttttcctgtt tggtcactga tgcctccgtg    3300 taaggggat ttctgttcat gggggtaatg ataccgatga acgagagag gatgctcacg     3360 atacgggtta ctgatgatga acatgcccgg ttactggaac gttgtgaggg taaacaactg    3420
gcggtatgga tgcggcggga ccagagaaaa atcactcagg gtcaatgcca gcgcttcgtt    3480
aatacagatg taggtgttcc acagggtagc cagcagcatc ctgcgatgca gatccggaac    3540
ataatggtgc agggcgctga cttccgcgtt tccagacttt acgaaacacg gaaaccgaag    3600
accattcatg ttgttgctca ggtcgcagac gttttgcagc agcagtcgct tcacgttcgc    3660
tcgcgtatcg gtgattcatt ctgctaacca gtaaggcaac cccgccagcc tagccgggtc    3720
ctcaacgaca ggagcacgat catgctagtc atgccccgcg cccaccggaa ggagctgact    3780
gggttgaagg ctctcaaggg catcggtcga gatcccggtg cctaatgagt gagctaactt    3840
acattaattg cgttgcgctc actgcccgct ttccagtcgg gaaacctgtc gtgccagctg    3900
cattaatgaa tcggccaacg cgcggggaga ggcggtttgc gtattgggcg ccagggtggt    3960
ttttcttttc accagtgaga cgggcaacag ctgattgccc ttcaccgcct ggccctgaga    4020
gagttgcagc aagcggtcca cgctggtttg ccccagcagg cgaaaatcct gtttgatggt    4080
ggttaacggc gggatataac atgagctgtc ttcggtatcg tcgtatccca ctaccgagat    4140
gtccgcacca acgcgcagcc cggactcggt aatggcgcgc attgcgccca gcgccatctg    4200
atcgttggca accagcatcg cagtgggaac gatgccctca ttcagcattt gcatggtttg    4260
ttgaaaaccg gacatggcac tccagtcgcc ttcccgttcc gctatcggct gaatttgatt    4320
```

```
gcgagtgaga tatttatgcc agccagccag acgcagacgc gccgagacag aacttaatgg    4380
gcccgctaac agcgcgattt gctggtgacc caatgcgacc agatgctcca cgcccagtcg    4440
cgtaccgtct tcatgggaga aaataatact gttgatgggt gtctggtcag agacatcaag    4500
aaataacgcc ggaacattag tgcaggcagc ttccacagca atggcatcct ggtcatccag    4560
cggatagtta atgatcagcc cactgacgcg ttgcgcgaga agattgtgca ccgccgcttt    4620
acaggcttcg acgccgcttc gttctaccat cgacaccacc acgctggcac ccagttgatc    4680
ggcgcgagat ttaatcgccg cgacaatttg cgacggcgcg tgcagggcca gactggaggt    4740
ggcaacgcca atcagcaacg actgtttgcc cgccagttgt tgtgccacgc ggttgggaat    4800
gtaattcagc tccgccatcg ccgcttccac ttttccccgc gttttcgcag aaacgtggct    4860
ggcctggttc accacgcggg aaacggtctg ataagagaca ccggcatact ctgcgacatc    4920
gtataacgtt actggtttca cattcaccac cctgaattga ctctcttccg ggcgctatca    4980
tgccataccg cgaaaggttt tgcgccattc gatggtgtcc gggatctcga cgctctccct    5040
tatgcgactc ctgcattagg aagcagccca gtagtaggtt gaggccgttg agcaccgccg    5100
ccgcaaggaa tggtgcatgc aaggagatgg cgcccaacag tccccggcc acggggcctg     5160 ccaccatacc cacgccgaaa caagcgctca tgagcccgaa gtggcgagcc cgatcttccc    5220
catcggtgat gtcggcgata taggcgccag caaccgcacc tgtggcgccg gtgatgccgg    5280
ccacgatgcg tccggcgtag cctaggatcg agatcgatct cgatcccgcg aaattaatac    5340
gactcactat a                                                         5351

<210> SEQ ID NO 6
<211> LENGTH: 3958
<212> TYPE: DNA
<213> ORGANISM: Artificial sequence
<220> FEATURE:
<223> OTHER INFORMATION: Synthetic DNA

<400> SEQUENCE: 6
gctaacagcg cgatttgctg gtgacccaat gcgaccagat gctccacgcc cagtcgcgta      60
ccgtcttcat gggagaaaat aatactgttg atgggtgtct ggtcagagac atcaagaaat     120
aacgccggaa cattagtgca ggcagcttcc acagcaatgg catcctggtc atccagcgga     180
tagttaatga tcagcccact gacgcgttgc gcgagaagat tgtgcaccgc cgctttacag     240
gcttcgacgc cgcttcgttc taccatcgac accaccacgc tggcacccag ttgatcggcg     300
cgagatttaa tcgccgcgac aatttgcgac ggcgcgtgca gggccagact ggaggtggca     360
acgccaatca gcaacgactg tttgcccgcc agttgttgtg ccacgcggtt gggaatgtaa     420
ttcagctccg ccatcgccgc ttccactttt ccccgcgttt tcgcagaaac gtggctggcc     480
tggttcacca cgcgggaaac ggtctgataa gagacaccgg catactctgc gacatcgtat     540
aacgttactg gtttcacatt caccaccctg aattgactct cttccgggcg ctatcatgcc     600
ataccgcgaa aggttttgcg ccattcgatg gtgtccggga tctcgacgct ctcccttatg     660
cgactcctgc attaggaagc agcccagtag taggttgagg ccgttgagca ccgccgccgc     720
aaggaatggt gcatgcaagg agatggcgcc caacagtccc cggccacgg ggcctgccac      780 catacccacg ccgaaacaag cgctcatgag cccgaagtgg cgagcccgat cttccccatc     840
ggtgatgtcg gcgatatagg cgccagcaac cgcacctgtg gcgccggtga tgccggccac     900
gatgcgtccg gcgtagccta ggatcgagat cgatctcgat cccgcgaaat taatacgact     960
```

```
cactatattg acaattaatc atccggctcg tataatgtgt ggaattgtga gcggataaca    1020
atttcacaca ggaaacagcg ccgctgagaa aaagcgaagc ggcactgctc tttaacaatt    1080
tatcagacaa tctgtgtggg cactcgaccg gaattatcga ttaactttat tattaaaaat    1140
tacctctaga aataattttg tttaacttta agaaggagat atacatatgg cagatctcaa    1200
ttggatatcg gccggccacg cgatcgctga cgtcggtacc ctcgagtctg gtaaagaaac    1260
cgctgctgcg aaatttgaac gccagcacat ggactcgtct actagtcgca gcttaattaa    1320
cctaaactgc tgccaccgct gagcaataac tagcataacc ccttgggggcc tctaaacggg    1380 tcttgagggg ttttttgcta gcaaaggag gagtcgacac tgcttccggt agtcaataaa    1440
ccggtaaacc agcaatagac ataagcggct atttaacgac cctgccctga accgacgacc    1500
gggtcatcgt ggccggatct tgcggcccct cggcttgaac gaattgttag acattatttg    1560
ccgactacct tggtgatctc gccttttcacg tagtggacaa attcttccaa ctgatctgcg    1620
cgcgaggcca agcgatcttc ttcttgtcca agataagcct gtctagcttc aagtatgacg    1680
ggctgatact gggccggcag gcgctccatt gcccagtcgg cagcgacatc cttcggcgcg    1740
attttgccgg ttactgcgct gtaccaaatg cgggacaacg taagcactac atttcgctca    1800
tcgccagccc agtcgggcgg cgagttccat agcgttaagg tttcatttag cgcctcaaat    1860
agatcctgtt caggaaccgg atcaaagagt tcctccgccg ctggacctac caaggcaacg    1920
ctatgttctc ttgcttttgt cagcaagata gccagatcaa tgtcgatcgt ggctggctcg    1980
aagatacctg caagaatgtc attgcgctgc cattctccaa attgcagttc gcgcttagct    2040
ggataacgcc acgaatgat gtcgtcgtgc acaacaatgg tgacttctac agcgcggaga    2100
atctcgctct ctccagggga agccgaagtt tccaaaaggt cgttgatcaa agctcgccgc    2160
gttgtttcat caagccttac ggtcaccgta accagcaaat caatatcact gtgtggcttc    2220
aggccgccat ccactgcgga gccgtacaaa tgtacggcca gcaacgtcgg ttcgagatgg    2280
cgctcgatga cgccaactac ctctgatagt tgagtcgata cttcggcgat caccgcttcc    2340
ctcatactct ccttttttca atattattga agcatttatc agggttattg tctcatgagc    2400
ggatacatat ttgaatgtat ttagaaaaat aaacaaatag ccagctcact cggtcgctac    2460
gctccgggcg tgagactgcg gcgggcgctg cggacacata caaagttacc cacagattcc    2520
gtggataagc aggggactaa catgtgaggc aaaacagcag ggccgcgccg gtggcgtttt    2580
tccataggct ccgccctcct gccagagttc acataaacag acgcttttcc ggtgcatctg    2640
tgggagccgt gaggctcaac catgaatctg acagtacggg cgaaacccga caggacttaa    2700
agatccccac cgtttccggc gggtcgctcc ctcttgcgct ctcctgttcc gaccctgccg    2760
tttaccggat acctgttccg cctttctccc ttacgggaag tgtggcgctt tctcatagct    2820
cacacactgg tatctcggct cggtgtaggt cgttcgctcc aagctgggct gtaagcaaga    2880 actcccgtt cagcccgact gctgcgcctt atccggtaac tgttcacttg agtccaaccc    2940
ggaaaagcac ggtaaaacgc cactggcagc agccattggt aactgggagt cgcagagga    3000 tttgtttagc taaacacgcg gttgctcttg aagtgtgcgc caaagtccgg ctacactgga    3060
aggacagatt tggttgctgt gctctgcgaa agccagttac cacggttaag cagttcccca    3120
actgacttaa ccttcgatca aaccacctcc ccaggtggtt ttttcgttta cagggcaaaa    3180
gattacgcgc agaaaaaaag gatctcaaga agatcctttg atcttttcta ctgaaccgct    3240
ctagatttca gtgcaattta tctcttcaaa tgtagcacct gaagtcagcc ccatacgata    3300
taagttgtaa ttctcatgtt agtcatgccc cgcgcccacc ggaaggagct gactgggttg    3360
```

```
aaggctctca agggcatcgg tcgagatccc ggtgcctaat gagtgagcta acttacatta    3420
attgcgttgc gctcactgcc cgctttccag tcgggaaacc tgtcgtgcca gctgcattaa    3480
tgaatcggcc aacgcgcggg gagaggcggt ttgcgtattg ggcgccaggg tggttttttct    3540 tttcaccagt gagacgggca acagctgatt gcccttcacc gcctggccct gagagagttg    3600
cagcaagcgg tccacgctgg tttgccccag caggcgaaaa tcctgtttga tggtggttaa    3660
cggcgggata taacatgagc tgtcttcggt atcgtcgtat cccactaccg agatgtccgc    3720
accaacgcgc agcccggact cggtaatggc gcgcattgcg cccagcgcca tctgatcgtt    3780
ggcaaccagc atcgcagtgg gaacgatgcc ctcattcagc atttgcatgg tttgttgaaa    3840
accggacatg gcactccagt cgccttcccg ttccgctatc ggctgaattt gattgcgagt    3900
gagatattta tgccagccag ccagacgcag acgcgccgag acagaactta atgggccc     3958
```

<210> SEQ ID NO 7
<211> LENGTH: 735
<212> TYPE: DNA
<213> ORGANISM: Escherichia coli

<400> SEQUENCE: 7

```
atggctgaga tgaaaaacct gaaaattgag gtggtgcgct ataacccgga agtcgatacc     60
gcaccgcata gcgcattcta tgaagtgcct tatgacgcaa ctacctcatt actggatgcg    120
ctgggctaca tcaaagacaa cctggcaccg gacctgagct accgctggtc ctgccgtatg    180
gcgatttgtg gttcctgcgg catgatggtt aacaacgtgc caaaactggc atgtaaaacc    240
ttcctgcgtg attacaccga cggtatgaag gttgaagcgt tagctaactt cccgattgaa    300
cgcgatctgg tggtcgatat gacccacttc atcgaaagtc tggaagcgat caaaccgtac    360
atcatcggca actcccgcac cgcggatcag ggtactaaca tccagacccc ggcgcagatg    420
gcgaagtatc accagttctc cggttgcatc aactgtggtt tgtgctacgc cgcgtgcccg    480
cagtttggcc tgaacccaga gttcatcggt ccggctgcca ttacgctggc gcatcgttat    540
aacgaagata gccgcgacca cggtaagaag gagcgtatgg cgcagttgaa cagccagaac    600
ggcgtatgga gctgtacttt cgtgggctac tgctccgaag tctgcccgaa acacgtcgat    660
ccggctgcgg ccattcagca gggcaaagta gaaagttcga agactttct tatcgcgacc    720 ctgaaaccac gctaa                                                    735
```

<210> SEQ ID NO 8
<211> LENGTH: 396
<212> TYPE: DNA
<213> ORGANISM: Escherichia coli

<400> SEQUENCE: 8

```
atgacgacta aacgtaaacc gtatgtacgg ccaatgacgt ccacctggtg gaaaaaattg     60 ccgtttttatc gcttttacat gctgcgcgaa ggcacggcgg ttccggctgt gtggttcagc    120
attgaactga ttttcgggct gtttgccctg aaaaatggcc cggaagcctg gcgggattc    180 gtcgactttt tacaaaaccc ggttatcgtg atcattaacc tgatcactct ggcggcagct    240
ctgctgcaca ccaaaacctg gttgaactg gcaccgaaag cggccaatat cattgtaaaa    300
gacgaaaaaa tgggaccaga gccaattatc aaaagtctct gggcggtaac tgtggttgcc    360
accatcgtaa tcctgtttgt tgccctgtac tggtaa                             396
```

<210> SEQ ID NO 9

```
<211> LENGTH: 1647
<212> TYPE: DNA
<213> ORGANISM: Escherichia coli

<400> SEQUENCE: 9
atgtcaaaca aacccttat  ctaccaggca cctttcccga tggggaaaga caataccgaa      60
tactatctac tcacttccga ttacgttagc gttgccgact tcgacggcga aaccatcctg     120
aaagtggaac cagaagccct gaccctgctg gcgcagcaag cctttcacga cgcttctttt     180
atgctccgcc cggcacacca gaaacaggtt gcggctattc ttcacgatcc agaagccagc     240
gaaaacgaca gtacgtggc  gctgcaattc ttaagaaact ccgaaatcgc cgccaaaggc     300
gtgctgccga cctgccagga taccggcacc gcgatcatcg tcggtaaaaa aggccagcgc     360
gtgtggaccg cggcggtga  tgaagaaacg ctgtcgaaag cgtctataa  cacctatatc     420
gaagataacc tgcgctattc acagaatgcg gcgctggaca tgtacaaaga ggtcaacacc     480
ggcactaacc tgcctgcgca aatcgacctg tacgcggtag atggcgatga gtacaaattc     540
ctttgcgttg cgaaaggcgg cggctctgcc aacaaaacgt atctctacca ggaaaccaaa     600
gccctgctga ctcccggcaa actgaaaaac ttcctcgtcg agaaaatgcg taccctcggt     660
actgcagcct gcccgccgta ccatatcgcg tttgtgattg gcggtacgtc tgcggaaacc     720
aacctgaaaa ccgtcaagtt agcaagcgct cactattacg atgaactgcc gacggaaggg     780
aacgaacatg gtcaggcgtt ccgcgatgtc cagctggaaa cggaactgct ggaagaggcc     840
cagaaactcg gtcttggcgc gcagtttggc ggtaaatact cgcgcacga  cattcgcgtt     900
atccgtctgc cacgtcacgg cgcatcctgc ccggtcggca tgggcgtctc ctgctccgct     960
gaccgtaaca ttaaagcgaa aatcaaccgc gaaggtatct ggatcgaaaa actggaacac    1020
aacccaggcc agtacattcc acaagaactg cgccaggccg tgaaggcga  agcggtgaaa    1080
gttgaccta  accgccgat  gaaagagatc ctcgcccagc tttcgcaata cccggtatcc    1140
actcgtttgt cgctcaccgg caccattatc gtgggccgag atattgcaca cgccaagctg    1200
aaagagctga ttgacgccgg taaagaactt ccgcagtaca tcaaagatca cccgatctac    1260
tacgcgggtc cggcgaaaac ccctgccggt tatccatcag gttcacttgg cccaaccacc    1320
gcaggccgta tggactccta cgtggatctg ctgcaatccc acggcggcag catgatcatg    1380
ctggcgaaag gtaaccgcag tcagcaggtt accgacgcgt gtcataaaca cggcggcttc    1440
tacctcggta gcatcggcgg tccggcggcg gtactggcgc agcagagcat caagcatctg    1500
gagtgcgtcg cttatccgga gctgggtatg gaagctatct ggaaaatcga agtagaagat    1560
ttcccggcgt ttatcctggt cgatgacaaa ggtaacgact tcttccagca aatcgtcaac    1620
aaacagtgcg cgaactgcac taagtaa                                        1647

<210> SEQ ID NO 10
<211> LENGTH: 990
<212> TYPE: DNA
<213> ORGANISM: Escherichia coli

<400> SEQUENCE: 10
atgaaactcg ccgtttatag cacaaaacag tacgacaaga agtacctgca acaggtgaac     60
gagtcctttg gctttgagct ggaattttt  gactttctgc tgacggaaaa aaccgctaaa    120
actgccaatg gctgcgaagc ggtatgtatt ttcgtaaacg atgacggcag ccgcccggtg    180
ctggaagagc tgaaaaagca cggcgttaaa tatatcgccc tgcgctgtgc cggtttcaat    240
aacgtcgacc ttgacgcggc aaaagaactg gggctgaaag tagtccgtgt tccagcctat    300
```

```
gatccagagg ccgttgctga acacgccatc ggtatgatga tgacgctgaa ccgccgtatt      360
caccgcgcgt atcagcgtac ccgtgatgct aacttctctc tggaaggtct gaccggcttt      420
actatgtatg gcaaaacggc aggcgttatc ggtaccggta aaatcggtgt ggcgatgctg      480
cgcattctga aaggttttgg tatgcgtctg ctggcgttcg atccgtatcc aagtgcagcg      540
gcgctggaac tcggtgtgga gtatgtcgat ctgccaaccc tgttctctga atcagacgtt      600
atctctctgc actgcccgct gacaccggaa actatcatc tgttgaacga agccgccttc      660
gaacagatga aaatggcgt gatgatcgtc aataccagtc gcggtgcatt gattgattct      720
caggcagcaa ttgaagcgct gaaaaatcag aaaattggtt cgttgggtat ggacgtgtat      780
gagaacgaac gcgatctatt ctttgaagat aaatccaacg acgtgatcca ggatgacgta      840
ttccgtcgcc tgtctgcctg ccacaacgtg ctgtttaccg gcaccaggc attcctgaca      900 gcagaagctc tgaccagtat ttctcagact acgctgcaaa acttaagcaa tctggaaaaa      960
ggcgaaacct gcccgaacga actggtttaa                                       990

<210> SEQ ID NO 11
<211> LENGTH: 2676
<212> TYPE: DNA
<213> ORGANISM: Escherichia coli

<400> SEQUENCE: 11
atggctgtta ctaatgtcgc tgaacttaac gcactcgtag agcgtgtaaa aaaagcccag       60
cgtgaatatg ccagtttcac tcaagagcaa gtagacaaaa tcttccgcgc cgccgctctg      120
gctgctgcag atgctcgaat cccactcgcg aaaatggccg ttgccgaatc cggcatgggt      180
atcgtcgaag ataaagtgat caaaaaccac tttgcttctg aatatatcta caacgcctat      240
aaagatgaaa aacctgtggt gttctgtctt gaagacgaca cttttggtac catcactatc      300
gctgaaccaa tcggtattat ttgcggtatc gttccgacca ctaacccgac ttcaactgct      360
atcttcaaat cgctgatcag tctgaagacc cgtaacgcca ttatcttctc cccgcacccg      420
cgtgcaaaag atgccaccaa caaagcggct gatatcgttc tgcaggctgc tatcgctgcc      480
ggtgctccga agatctgat cggctggatc gatcaacctt ctgttgaact gtctaacgca      540
ctgatgcacc acccagacat caacctgatc ctcgcgactg gtggtccggg catggttaaa      600
gccgcataca gctccggtaa accagctatc ggtgtaggcg cgggcaacac tccagttgtt      660
atcgatgaaa ctgctgatat caaacgtgca gttgcatctg tactgatgtc caaaaccttc      720
gacaacggcg taatctgtgc ttctgaacag tctgttgttg ttgttgactc tgtttatgac      780
gctgtacgtg aacgttttgc aacccacggc ggctatctgt tgcagggtaa agagctgaaa      840
gctgttcagg atgttatcct gaaaaacggt gcgctgaacg cggctatcgt ggtcagcca      900 gcctataaaa ttgctgaact ggcaggcttc tctgtaccag aaaacaccaa gattctgatc      960
ggtgaagtga ccgttgttga tgaaagcgaa ccgttcgcac atgaaaaact gtccccgact     1020
ctggcaatgt accgcgctaa agatttcgaa gacgcggtag aaaagcaga gaaactggtt     1080 gctatgggcg gtatcggtca tacctcttgc ctgtacactg accaggataa ccaaccggct     1140
cgcgtttctt acttcggtca gaaatgaaa acggcgcgta tcctgattaa caccccagcg     1200
tctcagggtg gtatcggtga cctgtataac ttcaaactcg caccttccct gactctgggt     1260
tgtggttctt ggggtggtaa ctccatctct gaaaacgttg gtccgaaaca cctgatcaac     1320
aagaaaaccg ttgctaagcg agctgaaaac atgttgtggc acaaacttcc gaaatctatc     1380
```

| | |
|---|---|
| tacttccgcc gtggctccct gccaatcgcg ctggatgaag tgattactga tggccacaaa | 1440 |
| cgtgcgctca tcgtgactga ccgcttcctg ttcaacaatg ttatgctga tcagatcact | 1500 |
| tccgtactga aagcagcagg cgttgaaact gaagtcttct tcgaagtaga agcggacccg | 1560 |
| accctgagca tcgttcgtaa aggtgcagaa ctggcaaact ccttcaaacc agacgtgatt | 1620 |
| atcgcgctgg tggtggttc cccgatggac gccgcgaaga tcatgtgggt tatgtacgaa | 1680 |
| catccggaaa ctcacttcga agagctggcg ctgcgcttta tggatatccg taaacgtatc | 1740 |
| tacaagttcc cgaaaatggg cgtgaaagcg aaaatgatcg ctgtcaccac cacttctggt | 1800 |
| acaggttctg aagtcactcc gtttgcggtt gtaactgacg acgctactgg tcagaaatat | 1860 |
| ccgctggcag actatgcgct gactccggat atggcgattg tcgacgccaa cctggttatg | 1920 |
| gacatgccga gtccctgtg tgctttcggt ggtctggacg cagtaactca cgccatggaa | 1980 |
| gcttatgttt ctgtactggc atctgagttc tctgatggtc aggctctgca ggcactgaaa | 2040 |
| ctgctgaaag aatatctgcc agcgtcctac cacgaagggt ctaaaaatcc ggtagcgcgt | 2100 |
| gaacgtgttc acagtgcagc gactatcgcg ggtatcgcgt ttgcgaacgc cttcctgggt | 2160 |
| gtatgtcact caatggcgca caaactgggt tcccagttcc atattccgca cggtctggca | 2220 |
| aacgccctgc tgatttgtaa cgttattcgc tacaatgcga acgacaaccc gaccaagcag | 2280 |
| actgcattca gccagtatga ccgtccgcag gctcgccgtc gttatgctga aattgccgac | 2340 |
| cacttgggtc tgagcgcacc gggcgaccgt actgctgcta agatcgagaa actgctggca | 2400 |
| tggctggaaa cgctgaaagc tgaactgggt attccgaaat ctatccgtga agctggcgtt | 2460 |
| caggaagcag acttcctggc gaacgtggat aaactgtctg aagatgcatt cgatgaccag | 2520 |
| tgcaccggcg ctaacccgcg ttacccgctg atctccgagc tgaaacagat tctgctggat | 2580 |
| acctactacg tcgtgatta tgtagaaggt gaaactgcag cgaagaaaga agctgctccg | 2640 |
| gctaaagctg agaaaaaagc gaaaaaatcc gcttaa | 2676 |

<210> SEQ ID NO 12
<211> LENGTH: 2130
<212> TYPE: DNA
<213> ORGANISM: Escherichia coli

<400> SEQUENCE: 12

| | |
|---|---|
| atggataaaa aagttttaac tgtttgtcct tactgtggcg ctggttgtaa tttatacttg | 60 |
| catgtaaaga atggcaaaat aattaaagca gagcctgcta atggtaggac aaatgaagga | 120 |
| tcactgtgtt taaaggaca cttttggttgg gatttttttaa acgatcctaa atatattgaca | 180 |
| tctagaatta aacatccgat gataagaaaa aacggagagc tagaagaggt aagctgggat | 240 |
| gaagctatta gttttacggc ttcaagattg tcacaaataa aagagaaata tggacctgat | 300 |
| tccataatgg gaacaggatg tgctagggt tctggaaacg aagcaaacta cataatgcaa | 360 |
| aagtttatga gggcggttat tggaaccaat aacgtagatc actgtgccag agtttgacat | 420 |
| gctccttctg tagccggtct ggcttacgtt ttaggaaatg gtgctatgtc aaatggtata | 480 |
| catgaaatag atgatacaga tttactactt attttttggat ataatggagc agcttcgcat | 540 |
| ccaatagttg ctaagagaat agttagggca aaacaaaagg gtgcaaaggt aatagttgta | 600 |
| gatccacgta taacagagtc tggtaggata gcagatttat ggctccctat aaaaaatgga | 660 |
| acaaatatgg ttcttgtaaa tactttgcc aacatactta taataaaca gttttataac | 720 |
| aaacaatatg tagaagatca tactgttggt tttgaagaat atagatctat agttgaaaat | 780 |
| tatactcctg aatatgcaga aaaagttact ggcatacctt cagaggatat agtagaagct | 840 |

```
atgaaaatgt actcaggtgc taaaaatgcc atgatattat atggtatggg agtatgtcaa      900
tttgctcaag ctgtagatgt agttaaggga ctagcttcta tagcattatt aactggtaat      960
tttggaagac ctaatgtagg tataggacct gtaagaggcc agaacaatgt tcaaggtgct     1020
tgtgatatgg gagcacttcc taatgtatac ccaggttatc aaagtgtaac tgacgatgca     1080
attagggaaa aatttgaaaa agcttggggt gttaaacttc caaacaaagt tggttatcac     1140
ctgacacaag ttcctgaatt aacgcttaaa gaggataaaa taaaggcata ttatataatg     1200
ggtgaagatc cagttcaaag tgatcctgat tctaatgaaa tgagagagac actggataaa     1260
atggaacttg taatagttca ggatatattt atgaataaaa ctgcactcca tgcagatgta     1320
attttacctt ccacgtcttg gggagaacat gaaggagtct tagttctgc agatagagga      1380 ttccagagat ttagaaaagc tgtagaacct aaggagatg ttaaaccaga ttgggaaata      1440
atttcaaaaa ttgcctgtgc tatgggttat aatatgcatt ataacaatac tgaggaaata     1500
tggaatgaac ttataaattt atgtccaaat ttcaaggag caacttataa agactcgaa       1560 gaattaggag gaatccaatg gccttgtcca tctgaaaatc atcctggaac ttcttatctc     1620
tacaaaggta taaatttaa tacacctact ggaaaagcaa acttatttgc agcagaatgg      1680
agacctcctg tagagcagac agataaagat tatccacttg ttctttctac agttagagaa     1740
gtaggacatt attctgtaag aacaatgaca ggaaactgta gggcacttca gcagttagcc     1800
gatgaaccag atatgtaca agttaatcca atggatgcaa aggctaaggg aataatagat      1860
ggtgagctta tgagaataag ttcacgaaga ggttctgtgg ttgcccgtgc acttattact     1920
gaaagggcaa ataaaggagc agtctatatg acctatcaat ggtgggtagg cgcatgtaat     1980
gaacttacat ctaataatct agatccagta tcaaaaactc ctgaattaaa gtattgtgca     2040
gtaaaaatag aagctataaa agatcagaaa gaagctgaaa agtttataaa agatcaatat     2100 gatctttaa agaaaaagat gaatgtttaa                                        2130
```

<210> SEQ ID NO 13
<211> LENGTH: 1959
<212> TYPE: DNA
<213> ORGANISM: Escherichia coli

<400> SEQUENCE: 13

```
atgagccaaa ttcacaaaca caccattcct gccaacatcg cagaccgttg cctgataaac       60
cctcagcagt acgaggcgat gtatcaacaa tctattaacg tacctgatac cttctggggc      120
gaacagggaa aaattcttga ctggatcaaa ccttaccaga aggtgaaaaa cacctccttt      180
gcccccggta atgtgtccat taaatggtac gaggacggca cgctgaatct ggcggcaaac      240
tgccttgacc gccatctgca agaaaacggc gatcgtaccg ccatcatctg ggaaggcgac      300
gacgccagcc agagcaaaca tatcagctat aaagagctgc accgcgacgt ctgccgcttc      360
gccaataccc tgctcgagct gggcattaaa aaggtgatg tggtggcgat ttatatgccg       420
atggtgccgg aagccgcggt tgcgatgctg gcctgcgccc gcattggcgc ggtgcattcg      480
gtgattttcg cggcttctc gccggaagcc gttgccgggc gcattattga ttccaactca      540
cgactggtga tcacttccga cgaaggtgtg cgtgccgggc agtattcc gctgaagaaa       600 aacgttgatg acgcgctgaa aaacccgaac gtcaccagcg tagagcatgt ggtggtactg     660
aagcgtactg gcgggaaaat tgactggcag aagggcgcg acctgtggtg gcacgacctg      720
gttgagcaag cgagcgatca gcaccaggcg gaagagatga acgccgaaga tccgctgttt     780
```

| | |
|---|---:|
| attctctaca cctccggttc taccggtaag ccaaaaggtg tgctgcatac taccggcggt | 840 |
| tatctggtgt acgcggcgct gacctttaaa tatgtctttg attatcatcc gggtgatatc | 900 |
| tactggtgca ccgccgatgt gggctgggtg accggacaca gttacttgct gtacggcccg | 960 |
| ctggcctgcg gtgcgaccac gctgatgttt gaaggcgtac ccaactggcc gacgcctgcc | 1020 |
| cgtatggcgc aggtggtgga caagcatcag gtcaatattc tctataccgc acccacggcg | 1080 |
| atccgcgcgc tgatggcgga aggcgataaa gcgatcgaag caccgaccg ttcgtcgctg | 1140 |
| cgcattctcg gttccgtggg cgagccaatt aacccggaag cgtgggagtg gtactggaaa | 1200 |
| aaaatcggca acgagaaatg tccggtggtc gatacctggt ggcagaccga aaccggcggt | 1260 |
| ttcatgatca ccccgctgcc tggcgctacc gagctgaaag ccggttcggc aacacgtccg | 1320 |
| ttcttcggcg tgcaaccggc gctggtcgat aacgaaggta accgctgga gggggccacc | 1380 |
| gaaggtagcc tggtaatcac cgactcctgg ccgggtcagg cgcgtacgct gtttggcgat | 1440 |
| cacgaacgtt ttgaacagac ctacttctcc accttcaaaa atatgtattt cagcggcgac | 1500 |
| ggcgcgcgtc gcgatgaaga tggctattac tggataaccg ggcgtgtgga cgacgtgctg | 1560 |
| aacgtctccg gtcaccgtct ggggacggca gagattgagt cggcgctggt ggcgcatccg | 1620 |
| aagattgcca agccgccgt agtaggtatt ccgcacaata ttaaaggtca ggcgatctac | 1680 |
| gcctacgtca cgcttaatca cggggaggaa ccgtcaccag aactgtacgc agaagtccgc | 1740 |
| aactgggtgc gtaaagagat tggcccgctg gcgacgccag acgtgctgca ctggaccgac | 1800 |
| tccctgccta aaacccgctc cggcaaaatt atgcgccgta ttctgcgcaa aattgcggcg | 1860 |
| ggcgatacca gcaacctggg cgatacctcg acgcttgccg atcctggcgt agtcgagaag | 1920 |
| ctgcttgaag agaagcaggc tatcgcgatg ccatcgtaa | 1959 |

<210> SEQ ID NO 14
<211> LENGTH: 1632
<212> TYPE: DNA
<213> ORGANISM: Escherichia coli

<400> SEQUENCE: 14

| | |
|---|---:|
| atgaataatt taaaaggttt agaattacta agaaatccct tcctcaataa aggtactgct | 60 |
| tttactcttg aagaaaggaa aaaatacgat ttaaccggtc ttcttccttg tgctgtaatg | 120 |
| actcttgaag agcaagaaaa ggtggtttat gaaaagctta atcaattga tgatgctttta | 180 |
| gataagcatt tttattttaat gaacatatac gatacaaata gaattctttt ctattatgtg | 240 |
| gtaaaaaaac atatcgttga acttcttcct atagtttata cccctactat tggagatgcc | 300 |
| gtaattaatt actctaagaa ttacgatact cctaaggatg ctgtcttctt atctataaac | 360 |
| catcccgaaa atataaaaaa atctatagaa gctgtttcca atgatttaga cgatattaag | 420 |
| cttattgttg ttactgatgg tgaaggtgtt cttggcatag gtgattgggg tattcaaggt | 480 |
| gtggatattt ccattggtaa acttgctgta tacactgtgg ctgccggtct taaccctaga | 540 |
| aatgtccttc ctattgttat tgatgcaggt actaataatg aagctcttct caatgatcct | 600 |
| ttttatgttg gcaataaaca caaaagagtt actggtgaaa agtactactc cttcattgat | 660 |
| gaattcgtaa aaacctgcac ctcactttc cctgatgttc ttcttcactg gaagactttt | 720 |
| ggacgcggca atgcaagcac tatacttgaa aaatacagaa ataacatatg cacctttaat | 780 |
| gatgatattc agggtacagg cgttatgatg gtagctgctc taaactctgt agcaaaagta | 840 |
| actaatactc ctattaaaaa tcacaaaata cttgtatttg gcggtggtac tgctggtatt | 900 |
| ggtgtatctg atcaaatact tttagaaaaa attagaagcg gtcttactct tgatgaggct | 960 |

```
ttaaaagatt tttatattgt agatcgtcag ggccttatca ctgaggatat gcaggattta    1020
actgaaggac agaaaaaata ttctagaaaa aaaggtgaat ttaaaaaacc tctaaaagac    1080
cttgcagaga tagttgctga agttaaacct actgtactaa ttggaacctc cggagttcac    1140
ggtgccttta ctgaagctgt tgttaaaaac atggcaaaat ccactgaaag accagctata    1200
atgccaattt ctaatccaac aaagcttgct gaagcaaaag ctgaggatat aataaaatgg    1260
tccgatggaa atgctcttgt ggttactgga agtccttctt ctcctgtaga atacaagggt    1320
gtaacctata caataggtca ggctaacaat gcccttcttt atcctggttt aggtcttgga    1380
atagttgttt ctaagtctaa gactgtttct gatggaatgc ttgctgctgc tgctcacggt    1440
gtttcttctt taatagacct ttccgtaaaa ggtgcaccta tgcttcctgt aatatcaaag    1500
cttagagaag cctcaaagct tgtagctact gctgtggtta agaagccgt taaagaaaat    1560 ttaaatcgtg cacctatagt tgatgctgaa aatgctgttg aaaatgaaat ttgggaacca    1620
tactataaat aa                                                        1632
```

<210> SEQ ID NO 15
<211> LENGTH: 69
<212> TYPE: DNA
<213> ORGANISM: Artificial sequence
<220> FEATURE:
<223> OTHER INFORMATION: Synthetic DNA

<400> SEQUENCE: 15

```
atggctgaga tgaaaaacct gaaaattgag gtggtgcgct ataacccggg tgtaggctgg    60
agctgcttc                                                            69
```

<210> SEQ ID NO 16
<211> LENGTH: 69
<212> TYPE: DNA
<213> ORGANISM: Artificial sequence
<220> FEATURE:
<223> OTHER INFORMATION: Synthetic DNA

<400> SEQUENCE: 16

```
ttaccagtac agggcaacaa acaggattac gatggtggca accacagtta tgggaattag    60
ccatggtcc                                                            69
```

<210> SEQ ID NO 17
<211> LENGTH: 20
<212> TYPE: DNA
<213> ORGANISM: Artificial sequence
<220> FEATURE:
<223> OTHER INFORMATION: Synthetic DNA

<400> SEQUENCE: 17

```
tggagtacag cgacgtgaag                                                20
```

<210> SEQ ID NO 18
<211> LENGTH: 20
<212> TYPE: DNA
<213> ORGANISM: Artificial sequence
<220> FEATURE:
<223> OTHER INFORMATION: Synthetic DNA

<400> SEQUENCE: 18

```
ggaatacgcg accaatgaag                                                20
```

<210> SEQ ID NO 19

```
<211> LENGTH: 69
<212> TYPE: DNA
<213> ORGANISM: Artificial sequence
<220> FEATURE:
<223> OTHER INFORMATION: Synthetic DNA

<400> SEQUENCE: 19
atgtcaaaca aacccttttat ctaccaggca cctttcccga tggggaaagg tgtaggctgg      60
agctgcttc                                                              69

<210> SEQ ID NO 20
<211> LENGTH: 69
<212> TYPE: DNA
<213> ORGANISM: Artificial sequence
<220> FEATURE:
<223> OTHER INFORMATION: Synthetic DNA

<400> SEQUENCE: 20
ttacttagtg cagttcgcgc actgtttgtt gacgatttgc tggaagaaga tgggaattag      60
ccatggtcc                                                              69

<210> SEQ ID NO 21
<211> LENGTH: 19
<212> TYPE: DNA
<213> ORGANISM: Artificial sequence
<220> FEATURE:
<223> OTHER INFORMATION: Synthetic DNA

<400> SEQUENCE: 21
tgtgagcgta tcgtgcgtc                                                   19

<210> SEQ ID NO 22
<211> LENGTH: 21
<212> TYPE: DNA
<213> ORGANISM: Artificial sequence
<220> FEATURE:
<223> OTHER INFORMATION: Synthetic DNA

<400> SEQUENCE: 22
cgtgaaatta caatcgcaaa c                                                21

<210> SEQ ID NO 23
<211> LENGTH: 69
<212> TYPE: DNA
<213> ORGANISM: Artificial sequence
<220> FEATURE:
<223> OTHER INFORMATION: Synthetic DNA

<400> SEQUENCE: 23
atgaaactcg ccgtttatag cacaaaacag tacgacaaga agtacctgcg tgtaggctgg      60
agctgcttc                                                              69

<210> SEQ ID NO 24
<211> LENGTH: 69
<212> TYPE: DNA
<213> ORGANISM: Artificial sequence
<220> FEATURE:
<223> OTHER INFORMATION: Synthetic DNA

<400> SEQUENCE: 24
ttaaaccagt tcgttcgggc aggtttcgcc tttttccaga ttgcttaaga tgggaattag      60
ccatggtcc                                                              69
```

```
<210> SEQ ID NO 25
<211> LENGTH: 18
<212> TYPE: DNA
<213> ORGANISM: Artificial sequence
<220> FEATURE:
<223> OTHER INFORMATION: Synthetic DNA

<400> SEQUENCE: 25
aacccacagc ccgagcgt                                                   18

<210> SEQ ID NO 26
<211> LENGTH: 21
<212> TYPE: DNA
<213> ORGANISM: Artificial sequence
<220> FEATURE:
<223> OTHER INFORMATION: Synthetic DNA

<400> SEQUENCE: 26
ggcttaccgt ttacgctttc c                                               21

<210> SEQ ID NO 27
<211> LENGTH: 69
<212> TYPE: DNA
<213> ORGANISM: Artificial sequence
<220> FEATURE:
<223> OTHER INFORMATION: Synthetic DNA

<400> SEQUENCE: 27
atggctgtta ctaatgtcgc tgaacttaac gcactcgtag agcgtgtaag tgtaggctgg     60
agctgcttc                                                             69

<210> SEQ ID NO 28
<211> LENGTH: 69
<212> TYPE: DNA
<213> ORGANISM: Artificial sequence
<220> FEATURE:
<223> OTHER INFORMATION: Synthetic DNA

<400> SEQUENCE: 28
ttaagcggat tttttcgctt ttttctcagc tttagccgga gcagcttcta tgggaattag     60
ccatggtcc                                                             69

<210> SEQ ID NO 29
<211> LENGTH: 19
<212> TYPE: DNA
<213> ORGANISM: Artificial sequence
<220> FEATURE:
<223> OTHER INFORMATION: Synthetic DNA

<400> SEQUENCE: 29
tcatcaccgc actgactat                                                  19

<210> SEQ ID NO 30
<211> LENGTH: 19
<212> TYPE: DNA
<213> ORGANISM: Artificial sequence
<220> FEATURE:
<223> OTHER INFORMATION: Synthetic DNA

<400> SEQUENCE: 30
tccttaactg atcggcatt                                                  19

<210> SEQ ID NO 31
<211> LENGTH: 55
<212> TYPE: DNA
```

```
<213> ORGANISM: Artificial sequence
<220> FEATURE:
<223> OTHER INFORMATION: Synthetic DNA

<400> SEQUENCE: 31
agatatacat atggcagatc tgatgaaaag tatactaact acttgtcctt attgt    55

<210> SEQ ID NO 32
<211> LENGTH: 47
<212> TYPE: DNA
<213> ORGANISM: Artificial sequence
<220> FEATURE:
<223> OTHER INFORMATION: Synthetic DNA

<400> SEQUENCE: 32
ggtttcttta ccagactcga gttaagcgtc tttacgcata ctctttt          47

<210> SEQ ID NO 33
<211> LENGTH: 46
<212> TYPE: DNA
<213> ORGANISM: Artificial sequence
<220> FEATURE:
<223> OTHER INFORMATION: Synthetic DNA

<400> SEQUENCE: 33
agatatacat atggcagatc tgatgagcca aattcacaaa cacacc           46

<210> SEQ ID NO 34
<211> LENGTH: 42
<212> TYPE: DNA
<213> ORGANISM: Artificial sequence
<220> FEATURE:
<223> OTHER INFORMATION: Synthetic DNA

<400> SEQUENCE: 34
ggtttcttta ccagactcga gttacgatgg catcgcgata gc               42

<210> SEQ ID NO 35
<211> LENGTH: 56
<212> TYPE: DNA
<213> ORGANISM: Artificial sequence
<220> FEATURE:
<223> OTHER INFORMATION: Synthetic DNA

<400> SEQUENCE: 35
agatatacat atggcagatc tgatgaataa tttaaaaggt ttagaattac taagaa    56

<210> SEQ ID NO 36
<211> LENGTH: 49
<212> TYPE: DNA
<213> ORGANISM: Artificial sequence
<220> FEATURE:
<223> OTHER INFORMATION: Synthetic DNA

<400> SEQUENCE: 36
ggtttcttta ccagactcga gttatctata gtatggttcc caaatttca        49
```